US010525125B2

(12) United States Patent
Nadeau

(10) Patent No.: US 10,525,125 B2
(45) Date of Patent: *Jan. 7, 2020

(54) MIXED ALLERGEN COMPOSITIONS AND METHODS FOR USING THE SAME

(71) Applicant: The Board of Trustees of the Leland Stanford Junior University, Stanford, CA (US)

(72) Inventor: Kari C. Nadeau, Los Altos Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/171,887

(22) Filed: Oct. 26, 2018

(65) Prior Publication Data

US 2019/0060445 A1    Feb. 28, 2019

Related U.S. Application Data

(63) Continuation of application No. 15/223,828, filed on Jul. 29, 2016, now Pat. No. 10,149,904, which is a continuation-in-part of application No. 15/048,609, filed on Feb. 19, 2016, now Pat. No. 10,064,936.

(60) Provisional application No. 62/119,014, filed on Feb. 20, 2015.

(51) Int. Cl.
| | | |
|---|---|---|
| *A61K 36/00* | (2006.01) | |
| *A61K 39/00* | (2006.01) | |
| *A61K 39/35* | (2006.01) | |
| *A61K 39/36* | (2006.01) | |
| *A61K 39/38* | (2006.01) | |
| *A61K 45/06* | (2006.01) | |
| *A61K 47/44* | (2017.01) | |
| *A61K 47/46* | (2006.01) | |
| *A61K 35/60* | (2006.01) | |
| *A61K 35/747* | (2015.01) | |
| *A61K 9/00* | (2006.01) | |
| *A61K 9/14* | (2006.01) | |
| *A61K 35/00* | (2006.01) | |

(52) U.S. Cl.
CPC ............ *A61K 39/35* (2013.01); *A61K 9/0053* (2013.01); *A61K 9/148* (2013.01); *A61K 35/60* (2013.01); *A61K 35/747* (2013.01); *A61K 45/06* (2013.01); *A61K 47/44* (2013.01); *A61K 47/46* (2013.01); *A61K 2035/115* (2013.01); *A61K 2039/54* (2013.01); *A61K 2039/542* (2013.01); *A61K 2039/55* (2013.01); *A61K 2039/57* (2013.01); *A61K 2039/572* (2013.01); *A61K 2039/575* (2013.01); *A61K 2039/70* (2013.01)

(58) Field of Classification Search
None
See application file for complete search history.

(56) References Cited

U.S. PATENT DOCUMENTS

| | | |
|---|---|---|
| 4,031,199 A | 6/1977 | Nieschulz et al. |
| 5,520,950 A | 5/1996 | Rosenplenter |
| 6,986,912 B2 | 1/2006 | Kramer |
| 7,048,928 B2 | 5/2006 | Loria et al. |
| 7,595,081 B1 | 9/2009 | Bellar |
| 8,524,242 B2 | 9/2013 | Saito et al. |
| 8,652,485 B2 | 2/2014 | Hafner et al. |
| 8,802,056 B2 | 8/2014 | Shea |
| 9,198,869 B2 | 12/2015 | Walser et al. |
| 9,271,899 B2 | 3/2016 | Francois |
| 9,273,129 B2 | 3/2016 | Simon |
| 9,345,761 B2 | 5/2016 | Esch |
| 9,402,896 B2 | 8/2016 | Tang |
| 9,481,716 B2 | 11/2016 | Clark et al. |
| 9,526,781 B2 | 12/2016 | Koppelman et al. |
| 9,539,318 B2 | 1/2017 | Dupont et al. |
| 9,731,003 B2 | 8/2017 | Nadeau |
| 9,744,230 B2 | 8/2017 | Hearl et al. |
| 9,808,517 B2 | 11/2017 | Putnam et al. |
| 10,064,936 B2 | 9/2018 | Nadeau |
| 10,143,742 B2 | 12/2018 | Nadeau |
| 10,149,904 B2 | 12/2018 | Nadeau |
| 10,166,286 B2 | 1/2019 | Nadeau |
| 2007/0202211 A1 | 8/2007 | Altom et al. |
| 2009/0324650 A1 | 12/2009 | Legon et al. |
| 2010/0278880 A1 | 11/2010 | Legon et al. |
| 2011/0229523 A1 | 9/2011 | Koppelman et al. |

(Continued)

FOREIGN PATENT DOCUMENTS

| | | |
|---|---|---|
| CN | 102048077 A | 5/2011 |
| CN | 102 986 802 A | 3/2013 |

(Continued)

OTHER PUBLICATIONS

American Thoracic Society (2016) "Early introduction of allergenic foods reduces risk of food sensitization," (1 page).
Begin et al. (2014) "Phase 1 results of safety and tolerability in a rush oral immunotherapy protocol to multiple foods using Omalizumab," Allergy Asthma Clin. Immunol., 10(1): 7 (10 pages).
Begin et al. (2014) "Safety and feasibility of oral immunotherapy to multiple allergens for food allergy,"Allergy Asthma Clin. Immunol., 10(1): 1 (8 pages).

(Continued)

*Primary Examiner* — Nora M Rooney
(74) *Attorney, Agent, or Firm* — Goodwin Procter LLP

(57) ABSTRACT

Mixed allergen compositions of one, two or more different allergens are provided. In some instances, the mixed allergen compositions include: a nut allergen; an animal allergen; and at least one of: a non-nut plant allergen; a biotic agent; and a vitamin. Also provided are methods of administering the mixed allergen compositions to a subject. The mixed allergen compositions find use in a variety of applications, including health maintenance, immune balance, gut balance, immune support, health improvement and therapeutic applications.

16 Claims, 10 Drawing Sheets

(56) References Cited

U.S. PATENT DOCUMENTS

| | | |
|---|---|---|
| 2012/0207815 A1 | 8/2012 | Benhamou et al. |
| 2013/0108706 A1 | 5/2013 | Svennevig |
| 2013/0218132 A1 | 8/2013 | Francois |
| 2013/0302374 A1 | 11/2013 | Esch |
| 2014/0010845 A1 | 1/2014 | Brimnes et al. |
| 2014/0271721 A1 | 9/2014 | Walser et al. |
| 2015/0050301 A1 | 2/2015 | Kettner et al. |
| 2015/0150956 A1 | 6/2015 | Henot et al. |
| 2015/0343075 A1 | 12/2015 | Raff |
| 2016/0030553 A1 | 2/2016 | Legon |
| 2016/0051593 A1 | 2/2016 | Raff |
| 2016/0051639 A1 | 2/2016 | Raff |
| 2016/0206731 A1 | 7/2016 | Francois |
| 2016/0228539 A1 | 8/2016 | Nelson et al. |
| 2016/0263212 A1 | 9/2016 | Friedman et al. |
| 2016/0324955 A1 | 11/2016 | Benhamou et al. |
| 2016/0331834 A1 | 11/2016 | Mondoulet et al. |
| 2017/0100476 A1 | 4/2017 | Legon et al. |
| 2017/0112919 A1 | 4/2017 | Nadeau |
| 2017/0112920 A1 | 4/2017 | Nadeau |
| 2017/0112921 A1 | 4/2017 | Nadeau |
| 2017/0151325 A1 | 6/2017 | Benhamou et al. |
| 2017/0304432 A1 | 10/2017 | Hearl et al. |
| 2017/0333386 A1 | 11/2017 | Lila et al. |
| 2017/0360922 A1 | 12/2017 | Turke |
| 2018/0020712 A1 | 1/2018 | Brown |
| 2018/0177895 A1 | 6/2018 | Mills et al. |
| 2019/0038741 A1 | 2/2019 | Nadeau |
| 2019/0060444 A1 | 2/2019 | Nadeau |

FOREIGN PATENT DOCUMENTS

| | | |
|---|---|---|
| CN | 104273238 A | 1/2015 |
| WO | WO-2001040264 | 6/2001 |
| WO | WO-2013078510 A1 | 6/2013 |
| WO | WO-2015042402 A1 | 3/2015 |
| WO | WO-2015185684 A1 | 12/2015 |
| WO | WO-2016134291 A2 | 8/2016 |
| WO | WO-2017048860 A1 | 3/2017 |
| WO | WO-2017139558 A1 | 8/2017 |

OTHER PUBLICATIONS

Begin et al. (2016) "Erratum to: Safety and feasibility of oral immunotherapy to multiple allergens for food allergy," Allergy Asthma Clin. Immunol., 12: 28 (1 page).

Bunyavanich et al. (2014) "Peanut, milk, and wheat intake during pregnancy is associated with reduced allergy and asthma in children," J. Allergy Clin. Immunol., 133(5): 1373-82.

Chinthrajah et al. (2016) "Molecular and cellular mechanisms of food allergy and food tolerance," J. Allergy Clin. Immunol., 137(4):984-97.

Choi et al. (2007) "Consumer-Based Optimization of a Third-Generation Product Made from Peanut and Rice Flour," Journal of Food Science, 72(7): S443-S449.

Cuello-Garcia et al. (2015) "Probiotics for the prevention of allergy: A systematic review and meta-analysis of randomized controlled trials," J. Allergy Clin. Immunol., 136(4):952-61.

Du Toit et al. (2008) "Early consumption of peanuts in infancy is associated with a low prevalence of peanut allergy," J. Allergy Clin. Immunol., 122(5): 984-991.

Du Toit et al. (2015) "Randomized Trial of Peanut Consumption in Infants at Risk for Peanut Allergy," N. Engl. J. Med., 372(9):803-13.

Du Toit et al. (2016) "Effect of Avoidance on Peanut Allergy after Early Peanut Consumption," N. Engl. J. Med., 374(15):1435-43.

Du Toit et al. (2016) "Prevention of food allergy," J. Allergy Clin. Immunol., 137(4):998-1010.

Dyer et al. (2015) "Epidemiology of childhood peanut allergy," Allergy Asthma Proc., 36(1):58-64.

Egg Nutritional Information. https://en.wikipedia.org/wiki/Egg_as_food.

Extended European Search Report for European Application No. 16753171.4, dated Jun. 11, 2018 (8 pages).

Favorite Brand Name Recipe Cookbook. Beekman House, New York 1991, pp. 290 and 296 (Cherry Winks and Shredded Wheat Cookies).

Feeney et al. (2016) "Impact of peanut consumption in the LEAP Study: Feasibility, growth, and nutrition," J. Allergy Clin. Immunol., 138(4):1108-1118.

Frazier et al. (2013) "Prospective Study of Peripregnancy Consumption of Peanuts or Tree Nuts by Mothers and the Risk of Peanut or Tree Nut Allergy in Their Offspring," JAMA Pediatr., 168(2):156-162.

Gupta et al. (2011) "The prevalence, severity, and distribution of childhood food allergy in the United States," Pediatrics. 128(1):e9-17.

Gupta et al. (2013) "Factors associated with reported food allergy tolerance among US children," Ann. Allergy Asthma Immunol., 111(3):194-198.

Gupta et al. (2013) "The economic impact of childhood food allergy in the United States," JAMA Pediatr., 167(11):1026-31.

Howard et al. (2010) "Analysis of Ingredient Functionality and Formulation Optimization of an Instant Peanut Beverage Mix," Journal of Food Science, 75(1): S8-S19.

Howard et al. (2011) "Analysis of Ingredient Functionality and Formulation Optimization of Pasta Supplemented with Peanut Flour" Journal of Food Science, 76(1): E40-E47.

http://allergen.org/search.php?allergensource=peanut&searchsource=Search.

International Search Report for PCT/US2016/018731, dated Aug. 22, 2016 (5 pages).

Katz et al. (2010) "Early exposure to cow's milk protein is protective against IgE-mediated cow's milk protein allergy," J. Allergy Clin. Immunol., 126(1):77-82.

Kim et al. (2016) "Dietary antigens limit mucosal immunity by inducing regulatory T cells in the small intestine," Science, 351(6275):858-63.

Koplin et al. (2010) "Can early introduction of egg prevent egg allergy in infants? A population-based study," J. Allergy Clin. Immunol., 126(4):807-13.

Koplin et al. (2016) "Understanding the feasibility and implications of implementing early peanut introduction for prevention of peanut allergy," J. Allergy Clin. Immunol., 138(4):1131-1141.

Kristensen et al. (2016) "Alterations in fecal microbiota composition by probiotic supplementation in healthy adults: a systematic review of randomized controlled trials," Genome Med., 8(1):52.

Kull et al. (2006) "Fish consumption during the first year of life and development of allergic diseases during childhood," Allergy, 61: 1009-1015.

Lau et al. (2012) "Parent report of childhood shellfish allergy in the United States," Allergy Asthma Proc., 33(6):474-80.

Mosha et al. (2004) "Nutritional value and acceptability of homemade maize/sorghum-based weaning mixtures supplemented with rojo bean flour, ground sardines and peanut paste," International Journal of Food Sciences and Nutrition, 55(4): 301-315.

Nwaru et al. (2010) "Age at the Introduction of Solid Foods During the First Year and Allergic Sensitization at Age 5 Years," Pediatrics, 125(1):50-9.

Nwaru et al. (2013) "Timing of infant feeding in relation to childhood asthma and allergic diseases," J. Allergy Clin. Immunol., 131(1): 78-86.

Otani et al. (2014) "Multiple-allergen oral immunotherapy improves quality of life in caregivers of food-allergic pediatric subjects," Allergy Asthma Clin. Immunol., 10(1):25 (7 pages).

Ozdemir (2010) "Various effects of different probiotic strains in allergic disorders: an update from laboratory and clinical data," Clin. Exp. Immunol., 160(3):295-304.

Perkin et al. (2016) "Randomized Trial of Introduction of Allergenic Foods in Breast-Fed Infants," N. Engl. J. Med., 374(18):1733-43.

Prinyawiwatkul et al. (1993) "Optimization of Sensory Qualities of an Extruded Snack Based on Cornstarch and Peanut Flour," Lebensm.-Wiss. u.—Technol. (26(5): 393-399.

Reilly et al. (2016) "The Gluten-Free Diet: Recognizing Fact, Fiction, and Fad," J. Pediatr., 175:206-10.

(56) References Cited

OTHER PUBLICATIONS

Reisacher, et al. (2016) "Oral mucosal immunotherapy for allergic rhinitis: A pilot study," Allergy Rhinol., 7(1):21-8.
Rudders et al. (2015) "Sunlight, vitamin D and food allergy," Curr. Opin. Allergy Clin. Immunol., 15(4):350-7.
Ryan et al. (2016) "Successful immunotherapy induces previously unidentified allergen-specific CD4+ T-cell subsets," Proc. Natl. Acad. Sci. U.S.A., 113(9):E1286-95.
Shaikh et al. (1993) "A retrospective study on the safety of immunotherapy in pregnancy," Clin. Exp. Allerg. 23(10): 857-860.
Shredded wheat nutritional information, 2017.
Syed et al. (2014) "Peanut oral immunotherapy results in increased antigen-induced regulatory T-cell function and hypomethylation of forkhead box protein 3 (FOXP3)," J. Allergy Clin. Immunol., 133(2):500-10.
Takagi et al. (2005) "A rice-based edible vaccine expressing multiple T cell epitopes including oral tolerance for inhibition of Th2-mediated IgE responses," PNAS, 102(48): 17525-17530.
The Journal of Pediatrics (2016) "The Gluten-Free Diet in Children: Do the Risks Outweigh the Benefits?" (2 pages).
Tran et al. (2016) "The Effects of Infant Feeding Practices on Food Sensitization in a Canadian Birth Cohort," American Thoracic Society 2016 International Conference, Session: D31 Novel Mechanisms of Allergy and Airway Inflammation, Abstract 8568 (2 pages).
Walnut Nutritional Information. https://en.wikipedia.org/wiki/Walnut.
Warren et al. (2013) "The epidemiology of milk allergy in US children," Ann. Allergy Asthma Immunol., 110(5):370-4.
Weinstock (2016) "A Glimpse of Microbial Power in Preventive Medicine," JAMA Pediatr. 170(1):11.
Written Opinion for PCT/US2016/018731, dated Aug. 2, 2016 (6 pages).
Zolkipli et al. (2015) "Randomized controlled trial of primary prevention of atopy using house dust mite allergen oral immunotherapy in early childhood," J. Allergy Clin. Immunol., 136(6):1541-7.
U.S. Appl. No. 15/048,609, Mixed Allergen Compositions and Methods for Using the Same, filed Feb. 19, 2016.
U.S. Appl. No. 15/223,812, Mixed Allergen Compositions and Methods for Using the Same, filed Jul. 29, 2016.
U.S. Appl. No. 15/223,828, Mixed Allergen Compositions and Methods for Using the Same, filed Jul. 29, 2016.
U.S. Appl. No. 15/224,004, Mixed Allergen Compositions and Methods for Using the Same, filed Jul. 29, 2016.
U.S. Appl. No. 15/347,260, Mixed Allergen Compositions and Methods for Using the Same, filed Nov. 9, 2016.
U.S. Appl. No. 15/989,741, Mixed Allergen Compositions and Methods for Using the Same, filed May 25, 2018.
U.S. Appl. No. 16/171,874, Mixed Allergen Compositions and Methods for Using the Same, filed Oct. 26, 2018.

MIXED ALLERGEN COMPOSITIONS AND METHODS FOR USING THE SAME

RELATED APPLICATIONS

This application is a continuation of U.S. patent application Ser. No. 15/223,828, filed Jul. 29, 2016, which is a continuation-in-part of U.S. patent application Ser. No. 15/048,609, filed Feb. 19, 2016 (U.S. Pat. No. 10,064,936, issued Sep. 4, 2018), which claims priority to U.S. patent application Ser. No. 62/119,014, filed Feb. 20, 2015; each of which is hereby incorporated by reference in their entirety.

BACKGROUND

Allergy is a disorder of the immune system and is characterized by the occurrence of allergic reactions to normally harmless environmental substances. Allergies are caused by allergens, which may be present in a wide variety of sources, including but not limited to pollens or other plant components, dust, molds or fungi, foods, additives, latex, transfusion reactions, animal or bird danders, insect venoms, radiocontrast medium, medications or chemicals. Common allergic reactions include eczema, hives, hay fever, asthma, and reactions to venoms. Mild allergies like hay fever are highly prevalent in the human population and cause symptoms such as allergic conjunctivitis, itchiness, and runny nose. In some people, severe allergies to environmental or dietary allergens or to medication may result in life-threatening anaphylactic reactions and potentially death, if left untreated. Allergic reactions can occur in three distinct patterns: a) an early phase reaction or acute response, b) late phase reactions and c) potentially chronic allergic inflammation. The early phase of the allergic reaction typically occurs within minutes, or even seconds, following a first allergen exposure, where this early phase is also commonly referred to as the immediate allergic reaction. In the early stages of allergy, a hypersensitivity reaction against an allergen, encountered for the first time, causes a response in Th2 cells, which are a subset of T cells that produce the cytokine interleukin-4 (IL-4). The Th2 cells interact with B cells (lymphocytes that produce antibodies against antigens) and, coupled with the effects of IL-4, stimulate the B cells to begin production and secretion of Immunoglobulin E (IgE).

IgE plays an important role in allergies and allergic reactions. Upon introduction of an allergen, B cells of the respective subject produce large amounts of IgE. The IgE elicits an immune response by binding onto receptors found on basophils and mast cells. When activated, these cells release chemical mediators such as histamine and cytokines that cause the characteristic symptoms of allergy.

A food allergy is an adverse immune response to a food allergen, e.g., a food protein. Common food allergens are found in shellfish, peanuts, tree nuts, fish, milk, eggs, soy and fresh fruits such as strawberries, mango, banana, and apple Immunoglobulin E (IgE)-mediated food allergies are classified as type-I immediate hypersensitivity reactions. These allergic reactions have an acute onset (from seconds to one hour) and the accompanying symptoms may include angioedema (soft tissue swelling of the eyelids, face, lips, tongue, larynx and trachea); hives; itching of the mouth, throat, eyes, or skin; gastrointestinal symptoms such as nausea, vomiting, diarrhea, stomach cramps, or abdominal pain; rhinorrhea or nasal congestion; wheezing, shortness of breath, or difficulty swallowing; and even anaphylaxis, a severe, whole-body allergic reaction that can result in death.

Gupta, et al. (PEDIATRICS Vol. 128 No. 1 Jul. 1, 2011 pp. e9-e17) demonstrated that 1 out of 12 children under the age of 21 years of age have a doctor's diagnosis of food allergies. This epidemic has been reported to be doubling every 10 years for certain nuts (CDC 2009). Moreover, there are still deaths that occur every year due fatal food allergies. Importantly, over S24 billion is spent per year on health care/care costs for food allergic reactions (Gupta, et al. JAMA PEDIATRICS November 2013, Vol. 167, No. 11). This cost is largely due to about 90,000 visits to the ER per year in the U.S. due to food induced anaphylactic symptoms.

SUMMARY

Mixed allergen compositions of two or more different allergens are provided. In some instances, the mixed allergen compositions include: a nut allergen; an animal allergen; and at least one of: a non-nut plant allergen; a biotic agent; and a vitamin. Also provided are methods of administering the mixed allergen compositions to a subject. The mixed allergen compositions find use in a variety of applications, including health maintenance, immune balance, gut balance, immune support, health improvement and therapeutic applications.

DETAILED DESCRIPTION

Figure 1:
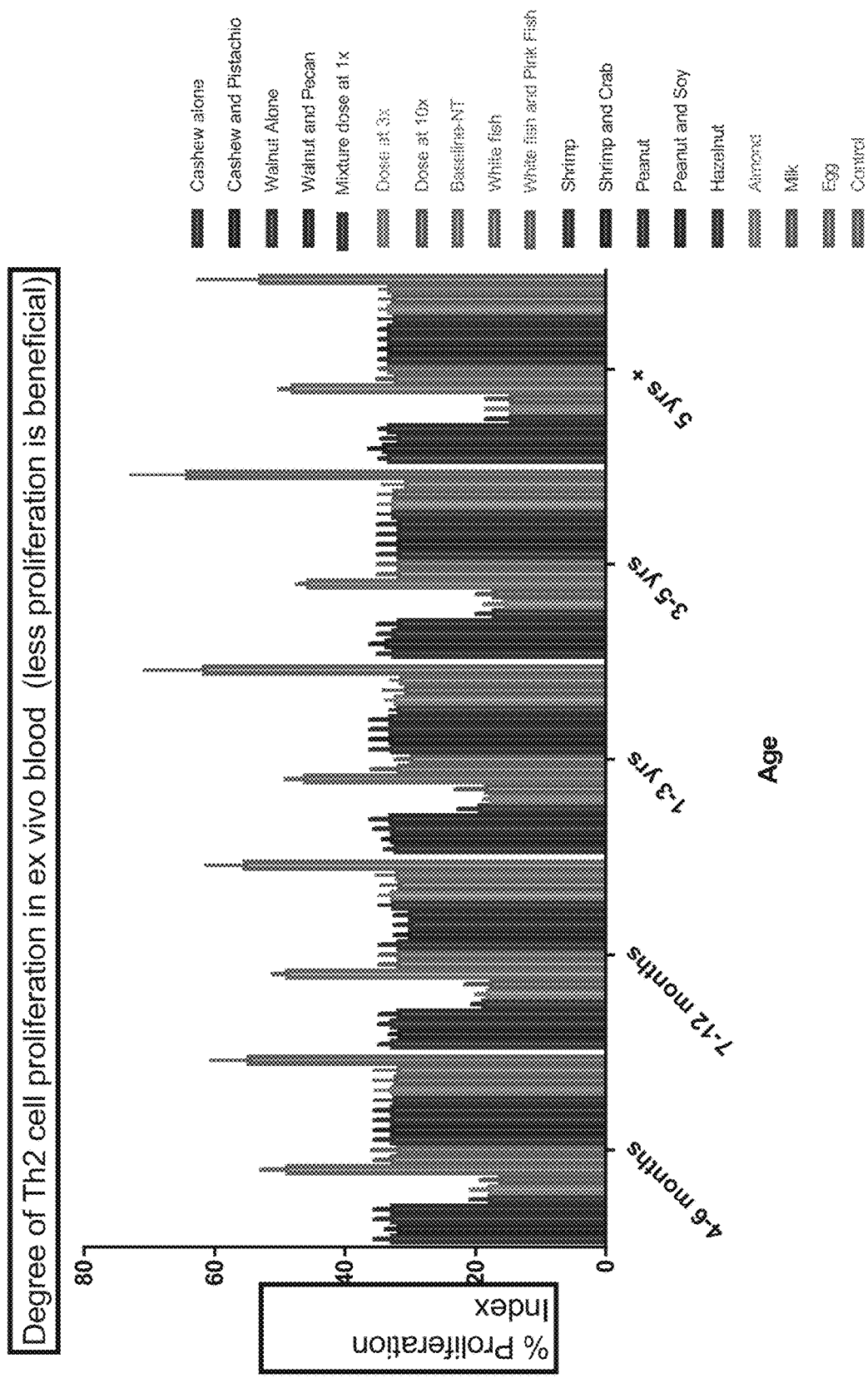
FIG. 1 depicts Th2 cell proliferation in ex vivo blood samples from subjects fed different food allergen mixtures (units are cells/mL). (It is noted that with respect to each of FIGS. 1 to 6 and 9 to 10, for each group of bars on the graphs the order of test compositions from left to right corresponds to the order of test compositions listed in the column at the right of the figure from top to bottom. As such, in FIG. 1, 4-6 months group, the bars from left to right are the data for each of the compositions tested from top to bottom in the column at the right hand side of the figure that lists the test compositions)

Mixed allergen compositions of two or more different allergens are provided. Mixed allergen compositions described herein comprise, e.g., 2 to 20 or more (e.g., 2 to 100 or more) different allergens, and optionally a vitamin such as a vitamin selected from vitamin D, E, B6, C, A or combinations thereof. In some instances, the mixed allergen compositions include: a nut allergen; an animal allergen; and at least one of: a non-nut plant allergen; a biotic agent; and a vitamin. In certain embodiments, a composition may comprise allergens selected from the group consisting of shellfish, peanuts, tree nuts, fish, milk, egg, legume, grain, sesame, and fruit allergen. In further embodiments, a composition may comprise allergens or allergens mixes selected from the group consisting of cashew, pistachio, walnut, almond, pecan, chicken egg, cow milk, peanut, shrimp, salmon, wheat, cod, crab, soy, sesame protein allergens, and an allergen mix comprising two or more thereof. The mixed allergen compositions find use in a variety of applications, including health maintenance, immune balance, gut balance, immune support, health improvement and therapeutic applications.

Also provided are methods of administering the mixed allergen compositions to a subject. Described herein are methods, e.g., for treating one or more food allergies in a human subject with an existing food allergy, which, e.g., may comprise administering a composition comprising 2 to 20 or more (e.g., 2 to 100 more) different protein allergens. Further described are methods, e.g., for inhibiting symptoms of one or more food allergies in a human subject, which, e.g., may comprise administering a composition comprising 2 to 20 or more (e.g., 2 to 100 more) different protein allergens, and optionally a vitamin, such as a vitamin selected from vitamin D and vitamin C. Such methods are surprisingly efficacious in treating, e.g. symptoms of allergies, e.g., even as compared to a composition having a single protein allergen. Also provided are methods of reducing the probability of developing one or more allergies in an unborn child of a pregnant woman or a child of a nursing mother, and methods of reducing the probability of developing one or more allergies in a child having a developing immune system.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Mixed Allergen Compositions

As summarized above, aspects of the invention include mixed allergen compositions. By mixed allergen composition is meant a composition that includes two or more different allergens, where any two given allergens are different if they are distinct from each other, e.g., they are compounds described by different chemical formula or compositions described by different components (e.g., constituent compounds) and/or amounts thereof. The number of different allergens in a composition may vary, as desired. In certain embodiments, the mixed allergen compositions include 2 more different allergens, such as 3 or more different allergens, 4 or more different allergens, 5 or more different allergens, 6 or more different allergens, 7 or more different allergens, 8 or more different allergens, 9 or more different allergens, 10 or more different allergens, 15 or more different allergens, 20 or more different allergens, 25 or more different allergens, 30 or more different allergens, 40 or more different allergens, 50 or more different allergens, 75 or more different allergens, 100 or more different allergens, where in some instances the number of different allergens in a given composition is 100 or less, such as 75 or less, including 50 or less, e.g., 25 or less, 15 or less, including 10 or less. In certain embodiments, a composition may comprise 2 to 20 different protein allergens, or e.g., 2 to 100 different allergens, or e.g., 2 to 1000 different allergens. In further embodiments, a composition may comprise 6 to 20 different protein allergens/protein allergen compositions. In certain embodiments, a composition may consist essentially of 2 to 20 different protein allergens, or e.g., 2 to 100 different allergens, or e.g., 2 to 1000 different allergens.

Allergens present in the composition may vary, where in some instances the allergen present in the composition is one that induces an allergy in a susceptible subject. Allergens include any antigen, or active derivative thereof, that elicits a specific IgE response. Antigens include any substance that can stimulate the production of antibodies and can combine specifically with them. Antigenic determinants or epitopes are antigenic sites on a molecule. Allergens may have little or no intrinsic toxicity by themselves, but cause a pathological condition due to their ability to elicit an IgE-associated immune response, and, upon subsequent exposure, due to their ability to elicit IgE- and/or T cell-dependent hypersensitivity reactions. As such, an "allergen" includes any substance which is capable of stimulating a typical hypersensitivity reaction in atopic subjects. Allergens that may be present in a given mixed allergen composition include any substance found in a variety of different sources, such as but not limited to: foods, drugs, perfume, plants, the environment or biological systems (e.g., prokaryotic or eukaryotic cells or viruses), as well as chemical allergens. It is appreciated that reference to allergen or an allergen composition (e.g., such as part of a provided food product or composition) may each include a plurality of different proteins as found in the naturally occurring allergen (either raw or cooked). For example, a provided food product may include a peanut allergen composition (which would include substantially all peanut proteins present in e.g., defatted peanuts, ground peanuts, etc.)

Allergens of interest include nut allergens. Nut allergens are allergens that include one or more compounds found in nuts, e.g., dry fruits that include an edible kernel or meat enclosed in a woody or leathery shell. Nut allergens of interest include, but are not limited to: peanut allergens, e.g., rAra h 1, rAra h 2, rAra h 3, rAra h 8 PR-10, rAra h 9 LTP, peanut complete allergen (the phrase "complete allergen" as used herein refers to all possible antigenic components of a given food protein), etc.; brazil nut allergens, e.g., rBer e 1, brazil nut complete allergen, etc.; hazelnut or filbert allergens, e.g., rCor a 1 PR-10, rCor a 8 LTP, hazel nut complete allergen, nCor a 9, rCor a 14, etc.; walnut allergens, e.g., rJug r 1, rJug r 3 LTP, walnut complete allergen, etc.; cashew allergens; pistachio allergens, e.g., pistachio component allergens, pistachio complete allergen, etc.; pecan allergens, e.g., pecan component allergens, pecan complete allergen, etc.; tree nut component package allergens, such as one or more allergens from cashew nut, walnut, hazelnut, brazil nut; etc.

Allergens of interest include animal allergens. Animal allergens are allergens that include one or more compounds found in animals, including both vertebrates and invertebrates. Vertebrate animal allergens that may be present in mixed allergen compositions include avian allergens, such as egg allergens, e.g., nGal d 1 Ovomucoid, n Gal d 2 Ovalbumin, nGal d 3 Conalbumin, egg white complete allergen, etc.; mammalian allergens, such as milk allergens, e.g., nBos d 4 alpha-lactalbumin, nBos d 5 beta-lactoglobulin, nBos d 8 Casein, nBos d Lactoferrin, milk complete allergen, etc.; fish allergens, e.g., rCyp c 1, rGad c 1, cod complete allergen, white fish allergens, pink fish allergens, etc. Invertebrate animal allergens that may be present in mixed allergen compositions include: crustacean allergens, such as shrimp allergens, e.g., rPen a 1 tropomyosin, shrimp complete allergen, etc.; insect allergens, e.g., bee sting venom allergen, wasp sting venom allergen, mosquito bite allergen, etc.; and the like.

Allergens of interest include non-nut plant allergens, i.e., plant allergens that are not nut allergens. Plant allergens are allergens that include one or more compounds found in plants. Plant allergens of interest include: wheat allergens, e.g., rTri a 19 Omega-5 Gliadin, wheat complete allergen, gliadin wheat, rTri a 14 LTP, etc.; fruit allergens, e.g., kiwi allergens, e.g., rAct d 8 PR-10, kiwi complete allergen, etc.; vegetable allergens, e.g., carrot allergens, celery allergens etc., e.g., rApi g 1.01 PR-10, rPhl p 12, celery complete allergen, CCD MUXF3 from Bromelain, etc.; legume allergens, e.g., soy allergens, chickpea allergens, etc., e.g., rGly m 4 PR-10, soy complete allergen, nGly m 5 Beta-conglycinin, nGly m 6 Glycinin, etc.; stone fruit allergens, e.g., f419, f420, f421, f95, f242, o214 rPru p 1 PR-10, rPru p 3 LTP, stone fruit primary complete allergen, CCD MUXF3 from Bromelain, etc.; oat allergens, e.g., oat component allergens, oat complete allergen, etc.; seed allergens, e.g., sesame allergens, e.g., sesame seed component allergens, sesame see complete allergen, etc.

Additional types of allergens that may be present in mixed allergen compositions include, but are not limited to: non-food animal allergens, e.g., cats or dog fur and dander, cockroach calyx, dust mite excretion, etc.; drug allergens, e.g., penicillin, sulfonamides, salicylates, local anesthetics, etc.; mold spore allergens; latex allergens; metal allergens; plant pollen allergens, e.g., grass—ryegrass, timothy-grass, weeds—ragweed, plantago, nettle, *Artemisia, vulgaris, Chenopodium album*, sorrel, trees—birch alder, hazel, hornbeam, *aesculus*, willow, poplar, *platanus, tilia, olea*, etc.; etc.

In certain embodiments, a composition may comprise one, two, or more allergens each independently selected from the allergens disclosed in Examples 1 or 2 herein. For example, in certain embodiments, a composition may comprise one, two, or more allergens selected from a group consisting of cashew (e.g., finely ground cashew from "Wellbee's", Spring Valley, N.Y. 10977), pistachio (e.g., pistachio flour from "nuts.com", Cranford, N.J. 07016), walnut (e.g. roasted walnut from "Holmquist Hazelnut Orchards", Lynden Wash. 98264), pecan (e.g., ground pecan from "King Arthur Flour", Norwich, Vt., 05055), white fish (e.g., pacific cod from "Seattle Seafoods", Bellevue, Wash. 98008), pink fish (e.g., sockeye salmon from "Seattle Seafoods", Bellevue, Wash. 98008), shrimp (e.g., white shrimp from "Seattle Seafoods", Bellevue, Wash. 98008), peanut (e.g., defatted peanuts from "Byrd Mill Company", Ashland, Va. 23005), soy (e.g., stone ground soy from "Bob's Red Mill", Milwaukie, Oreg. 97222), hazelnut (e.g., natural hazelnuts from "Holmquist Hazelnut Orchards", Lynden Wash. 98264), almond (e.g., blanched almond flour from "Honeyville" Rancho Cucamonga, Calif. 91730), milk (e.g., organic non-fat dry milk powder from "Now Foods" Bloomingdale, Ill. 60108), egg (e.g., powdered egg whites with sodium lauryl sulphate as an anti-caking agent from "Honeyville Food Products", Honeyville, Utah 84314), crab (e.g., crab from "Seattle Seafoods", Bellevue, Wash. 98008), wheat (e.g., wheat flour from "Arrowhead Mills", USA. Boulder, Colo. 80301), and sesame (Sesame flour from "Dipasa", Brownsville, Tex. 78526), and optionally, vitamin D.

The amount of a given allergen in a mixed allergen composition may vary, as desired. In some instances, the amount of a given allergen ranges from about 1 to about 15,000 mg, about 5 to about 15,000 mg, about 10 to about 10,000 mg, about 15 to about 5,000 mg, about 10 to about 100 mg, or about 15 to about 100 mg. The weight percentage of a given allergen in a mixed allergen composition may vary, ranging in some instances from about 0.1 to about 99.9 wt. %, about 0.1 to about 15 wt. %, about 0.1 to about 99.9 wt. %, about 15 to about 99.9 wt. %, or about 25 to about 65 wt. %. The amount of a given allergen in a mixed allergen composition may be recited by total mass, or by protein mass, which may vary for a given allergen depending upon the weight percentage of protein in that allergen.

A mixed allergen composition may be a unit dosage composition, by which is meant that it is present in a composition that is configured to be administered to a subject as a single dose, which single dose may or may not be part of a dosing schedule made up of two or more unit dosages that are administered to a subject over a given a period of time. While the mass of a given unit dosage may vary, in some instances unit dosages have a mass ranging from 300 mg to 20 grams, such as 300 mg, 400 mg, 500 mg, 600 mg, 700 mg, 800 mg, 900 mg, 1000 mg (1 g), 1.5 g, 2 g, 3 g, 4 g, 5 g, 10 g, 15 g, 20 g, and anywhere in between. In certain embodiments, any two of the mixed allergens are present in equal parts, e.g., in a 1:1 ratio, such that each allergen is present in the composition in equal weight. In such embodiments where the mixed allergen composition includes three different allergens, the three different allergens are present in a 1:1:1 ratio. For example, a mixed allergen composition may include the following allergens in equal parts (e.g., 1:1:1 etc. ratio): walnut, hazelnut, shrimp, salmon, hen's egg, cow's milk, peanut, cashew, almond, and wheat (e.g., about 30 mg of protein each; about 90 mg of each protein; or about 300 mg of each protein). In certain embodiments, the mixed allergen composition comprises almond, cashew, walnut, hazelnut, peanut, soy, wheat, hen's egg, cow's milk, white fish, pink fish, shrimp, and sesame allergens in equal parts with a total estimated protein of 400 mg and 400 IU of vitamin D3.

In some embodiments, the mixed allergen compositions include a nut allergen and an animal allergen; and at least one of: a non-nut plant allergen; a biotic agent; and a vitamin. As such, in some embodiments, the mixed allergen compositions include a nut allergen, an animal allergen and a non-nut plant allergen. In such embodiments, the mixed allergen compositions may further include a biotic agent or vitamin or both a biotic agent and a vitamin. In some embodiments, the mixed allergen compositions include a nut allergen, an animal allergen, and further include a biotic agent. In such embodiments, the mixed allergen compositions may further include a vitamin. In some embodiments, the mixed allergen compositions include a nut allergen, an animal allergen, and further include a vitamin. In such embodiments, the mixed allergen compositions may further include a biotic agent.

Biotic agents may vary, and include both probiotics and prebiotics. A probiotic is generally a live eukaryotic or a prokaryotic organism which has a beneficial property when given to a subject. In one aspect, the probiotic complements the existing microflora in the subject. Hence, the probiotic agent is a live microorganism which can confer a health benefit to a host subject. The probiotic agent may be a culture of microorganisms or provided in a dietary supplement or may be freeze dried and reconstituted prior to use. A prebiotic is an agent that facilitates or confers growth, maintenance and/or beneficial properties of or on the subject's microflora. A prebiotic may include an oligosaccharide and soluble or insoluble fiber material. Examples of probiotic agents include, but are not limited to, species of *Lactobacillus* spp., *Escherichia* spp., *Bacillus* spp., *Bifidobacterium* spp., *Saccharomyces* spp. and *Streptococcus* spp. Specific probiotic agents that may be present in the mixed allergen compositions include: *Lactobacillus* spp., such as *Lactobacillus acidophilus*, *Lactobacillus casei*, *Lactobacillus casei Shirota*, *Lactobacillus casei immunitass*, *Lactobacillus johnsonii*, *Lactococcus lactis*, *Lactobacillus plantarum*, *Lactobacillus reuteri*, *Lactobacillus rhamnosus* (*lactobacillus GG*), *Lactobacillus salivarius* and *Lactobacillus helvetirus*. The probiotic microorganisms may be naturally occurring, attenuated or genetically modified to introduce new or to alter existing traits. In one embodiment, the probiotic has been genetically modified to introduce an allergen gene or part or fragment or portion thereof which is expressed to produce recombinant microorganisms which release or expose the subject's immune system to the allergen or an antigenic fragment thereof. Hence, the probiotic and allergen may be combined into a single component of the mixed allergen composition. When present, the amount of the biotic agent in the mixed allergen composition may vary. In some instances, the biotic agent is present in an amount ranging from 1.5 to 99.9 wt. %, such as 10 to 25 wt. %.

The mixed allergen compositions may include one or more vitamins, as desired. Vitamins that may be present in the compositions include, but are not limited to: vitamin A, e.g., in an amount ranging from 1 to 35,000 IU; vitamin C, e.g., in an amount ranging from 1 to about 1,000 mg; vitamin D, e.g., in an amount ranging from 1 to 4,000 IU; vitamin E, e.g., in an amount ranging from 1 to 450 IU; vitamin K, e.g., in an amount ranging from 1 to 250 mcg; vitamin B-1 (thiamin), e.g., in an amount ranging from 1 to 15 mg; vitamin B-2 (riboflavin), e.g., in an amount ranging from 1 to 17 mg; vitamin B-3 (niacin), e.g., in an amount ranging from 1 to 200 mg; vitamin B-5 (pantothenic acid), e.g., in an amount ranging from 1 to 100 mg; vitamin B-6 (pyridoxine), e.g., in an amount ranging from 1 to 30 mg; vitamin B-9 (folic acid), e.g., in an amount ranging from 1 to 4,000 mcg; vitamin B-12 (cobalamin), e.g., in an amount ranging from 1 to 250 mcg; vitamin H (biotin), e.g., in an amount ranging from 1 to 1,000 mcg of vitamin H (biotin); etc.; and combinations thereof.

The allergen or mixed allergen compositions of the invention may be present in different configurations. In some instances the allergen or mixed allergen composition is present in a solid configuration, e.g., as a powder, e.g., as a ground meal or flour. When present as a powder, the dimensions of the particles making up the powder may vary, ranging in some instances from 0.1 to 1000 microns, such as 1 to 500 microns.

Also provided are physiological acceptable compositions that include the mixed allergen compositions and a physiologically acceptable delivery vehicle. The mixed allergen compositions can be incorporated into a variety of formulations for administration to a subject. More particularly, the mixed allergen compositions can be formulated into physiological acceptable compositions by combination with appropriate, physiologically acceptable carriers or diluents, and may be formulated into preparations in solid, semi-solid, liquid or gaseous forms, such as tablets, capsules, powders, granules, ointments, solutions, suppositories, injections, inhalants and aerosols and topical compositions. The formulations may be designed for administration via a number of different routes, including oral, buccal, sublingual, rectal, parenteral, intraperitoneal, intradermal, transdermal, intracheal, etc., administration.

The physiological compositions may be in a form suitable for oral use, for example, as foods, tablets, troches, lozenges, aqueous or oily suspensions, dispersible powders or granules, emulsions, hard or soft capsules, or syrups or elixirs, gums, etc. Compositions intended for oral use may be prepared according to any convenient protocol for the manufacture of pharmaceutical compositions and such compositions may contain one or more agents selected from the group consisting of sweetening agents, flavoring agents, coloring agents and preserving agents in order to provide palatable preparations.

In certain embodiments the composition is a food product. Food products of interest include a disclosed mixed allergen composition in combination with a food delivery vehicle. By food delivery vehicle is meant a delivery vehicle that is a nourishing substance that is eaten, drunk, or otherwise taken into the body to sustain life, provide energy, promote growth, etc. Examples of food delivery vehicles or food products of interest include, but are not limited to: baby or infant formula, baby food (e.g., pureed food suitable for infant or toddler consumption), chips, cookies, breads, spreads, creams, yogurts, liquid drinks, chocolate containing products, candies, ice creams, cereals, coffees, pureed food products, baked food products, etc.

Also of interest as oral formulations are food supplements. Where the oral formulation is provided as a food supplement, the food supplement may further include one or more of a sweetener, a stabilizer, a flavoring or a colorant, etc. An oral formulation according to the present disclosure may be provided in the form of sugar-coated tablets or lozenges, pills, gelatin capsules, or syrups. Oral formulations may be provided as a bulk sample, e.g., a container having multiple doses in powder form that can be measured out by a subject, or in unit dose form, e.g., a pill, pouch, single use container, and the like.

Tablets may contain the active ingredient in admixture with non-toxic physiologically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the mixed allergen component is mixed with an inert solid diluent, for example, calcium carbonate, calcium phosphate or kaolin, or as soft gelatin capsules wherein the mixed allergen component is mixed with water or an oil medium, for example peanut oil, liquid paraffin, or olive oil.

Aqueous suspensions contain the mixed allergen component in admixture with excipients suitable for the manufacture of aqueous suspensions. Such excipients may include suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The physiologically acceptable compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The mixed allergen components can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The mixed allergen components can be utilized in aerosol formulation to be administered via inhalation. The compounds of the present invention can be formulated into pressurized acceptable propellants such as dichlorodifluoromethane, propane, nitrogen and the like.

Furthermore, the mixed allergen compositions can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Also of interest are topical compositions, e.g., where the mixed allergen composition is combined with a topical delivery vehicle component. The topical delivery vehicle component of the delivery compositions of the invention may vary, as desired, where the particular ingredients of a given delivery vehicle component will depend, at least in part, on the nature of the particular composition. Delivery compositions of interest include liquid formulations, such as lotions (liquids containing insoluble material in the form of a suspension or emulsion, intended for external application, including spray lotions) and aqueous solutions, semi-solid formulations, such as gels (colloids in which the disperse phase has combined with the dispersion medium to produce a semisolid material, such as a jelly), creams (soft solids or thick liquids) and ointments (soft, unctuous preparations), and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols or sticks.

The amount of mixed allergen composition that may be combined with the carrier materials to produce a single dosage form will vary depending upon the host treated and the particular mode of administration. For example, a unit formulation intended for the oral administration of humans may contain from 0.5 mg to 5 g of mixed allergen composition compounded with an appropriate and convenient amount of carrier material which may vary from about 0.1 to about 95 percent of the total composition, or e.g. about 0.1 to about 10 percent, about 0.1 to about 4 weight percent, or about 5 to about 95 percent of the total composition. It will be understood, however, that the specific dose level for any particular patient will depend upon a variety of factors including the age, body weight, general health, sex, diet, time of administration, route of administration, rate of excretion, drug combination and the severity of the particular disease undergoing therapy. As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. As described above "unit dosage forms," include physically discrete units suitable as unitary dosages for human and animal subjects, each unit containing a predetermined quantity of mixed allergen composition calculated in an amount sufficient to produce the desired effect in association with a pharmaceutically acceptable diluent, carrier or vehicle.

Methods

Aspects of the invention also include methods of administering a mixed allergen composition, e.g., as described above, to a subject. The administration route employed in a given method may vary, e.g., depending on the nature of the mixed allergen composition. As reviewed above, physiologically acceptable compositions that include a mixed allergen composition may be formulated for delivery to a subject using a variety of different administration routes, such as but not limited to: oral, buccal, sublingual, rectal, parenteral, intraperitoneal, intradermal, transdermal, intracheal, etc., administration. As such, aspects of the methods may include orally, buccaly, sublingually, rectally, parenterally, intraperitonealy, intradermally, transdermally, intracheally, etc., administering a mixed allergen composition or physiologically acceptable composition that includes the same, e.g., as described above, to a subject.

The methods described herein may be employed with a variety of different types of subjects, i.e., animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In embodiments of the invention, the subjects are humans. The subject may be infant, juveniles or adults, where in some instances the subject may be pregnant adults, e.g., as described in greater detail below. As such, in certain embodiments, the subject is a pediatric subject younger than 1 year of age, whereas in other embodiments the subject is older, e.g., 1 year old or more, 5 years old or more, etc., and including adults. In certain embodiments the pediatric subject is 1 month to 7 years old, e.g., 1 month to 1 year old, 6 months to 7 years old, 6 months to 1 year old, 2 years to 4 years old, or 3 to 7 years old. In certain embodiments, the pediatric subject is an unborn child of a pregnant woman or a child of a nursing mother.

The dosing schedule may vary as desired, and may depend on a number of different factors, e.g., purpose of the administration, age of the subject, condition of the subject, nature of the physiologically acceptable composition, etc. In certain embodiments, a mixed allergen composition or physiologically acceptable composition that includes the same is administered to a subject on an hourly basis, on an every few hours basis (e.g., every 2, 3, 4, 6 hours), on a daily basis, on a weekly basis, on a bi-weekly basis, on a monthly basis, one a bimonthly basis, on a quarter annual basis, on a semi-annual basis, on an annual basis, etc., for a treatment period of time, which treatment period of time may also vary, where in some instances the treatment period of time is 1 day or longer, 1 week or longer, 2 weeks or longer, 1 month or longer, 3 months or longer, 6 months or longer, 1 year or longer, 2 years or longer, 3 years or longer, 5 years or longer, 10 years or longer, etc., up to the life of the subject. In certain embodiments, the composition is administered to a subject for a time or frequency to allow sufficient time for the administration of the composition to inhibit the symptoms of food allergy in a subject.

In some embodiments, the methods are methods of increasing immune health of the subject. As the methods of these embodiments are methods of increasing the immune health of a subject, embodiments of such methods result in the subject being better able to have a healthy immune response to a given challenge Immune health or immune balance may be characterized as a state in the body where there is not an imbalance of inflammation. For example, when IgE is decreased and/or IgG4 increased in plasma and/or Th2 decreased (e.g., as described in greater detail below in the Examples section and accompanying figures). The magnitude of immune health enhancement may vary, where in some instances the magnitude is 2-fold or greater, e.g., 5-fold or greater, including 10-fold or greater, e.g., as compared to a suitable control.

In some embodiments, the methods are methods of increasing gut health of the subject. As the methods of these embodiments are methods of increasing the gut health of a subject, embodiments of such methods result in the subject having an enhanced maintenance of healthy microbiota or improving the resilience of microbiota, for instance, by reducing the numbers or colonization of pathogenic bacteria or viruses and by maintaining and improving the intestinal integrity and barrier function. Gut health or gut balance may be characterized as a state in the body where there is not an imbalance of inflammation. For example, when T cell proliferation is decreased (e.g., as described in greater detail below in the Examples section and accompanying figures). The magnitude of gut health enhancement may vary, where in some instances the magnitude is 2-fold or greater, e.g., 5-fold or greater, including 10-fold or greater, e.g., as compared to a suitable control.

In some embodiments, the methods are methods of enhancing wellness or maintaining immune balance of the subject. As the methods of these embodiments are methods of enhancing wellness of a subject, embodiments of such methods result in the subject having a quality or state of being healthy in body and mind. Wellness may be characterized as a state of the body where there is not an imbalance of immune problems (for example, less IgE, more IgG4, less cell inflammation (e.g., as described in greater detail below in the Examples section and accompanying figures). The magnitude of wellness enhancement may vary, where in some instances the magnitude is 2-fold or greater, e.g., 5-fold or greater, including 10-fold or greater, e.g., as compared to a suitable control.

In some embodiments, the methods are methods of at least decreasing the potential of the subject for developing an immune mediated condition, such as an immune-mediated inflammatory disease condition. By at least decreasing the potential of the subject for developing an immune mediated condition is meant that the probability of the subject for developing the immune mediated condition is reduced, such that the risk of the subject for developing the immune mediated condition is reduced. For example, to determine risk reduction, if 100 different individuals were administered the composition, 20% or more of the individuals would show a decrease in their immune markers, e.g., IgE, as compared to the control group. The magnitude of the decrease in potential may vary, where in some instances the magnitude is 2-fold or greater, e.g., 5-fold or greater, including 10-fold or greater, e.g., as compared to a suitable control. In some instances, the methods are methods of preventing the subject from developing an immune mediated condition. As such, the methods of the invention include administering a composition of the invention to a subject that is not known to have or does not have an immune mediated condition. While the subject may not have or may not be known to have the immune mediated condition, the subject may be one that is suspected to be or known to be at risk of developing the immune mediated condition.

Aspects of the invention further include methods of treating a subject for an immune mediated condition. By treating or treatment is meant at least an amelioration of one or more symptoms associated with the disease condition, e.g., immune mediated condition, afflicting the subject, where amelioration is used in a broad sense to refer to at least a reduction in the magnitude of a parameter, e.g., symptom, associated with the pathological condition being treated, etc. As such, treatment also includes situations where the pathological condition, or at least symptoms associated therewith, are completely inhibited, e.g., prevented from happening, or stopped, e.g., terminated, such that the subject no longer suffers from the pathological condition, or at least the symptoms that characterize the pathological condition.

Treatment may also manifest in the form of a modulation of a surrogate marker of the disease condition. For example, where the target condition is an allergy, e.g., as described below, Th2 cell proliferation may be reduced, e.g., as determined using the assay described in the Examples Section, below. The magnitude of Th2 cell proliferation reduction may vary, and in certain instances may range from 1.2× to 10×, such as 2× to 4×. Where the target condition is an allergy, e.g., as described below, specific IgG4 levels may be increased, e.g., as determined using the assay described in the Examples Section, below. The magnitude of IgG4 level increase may vary, and in certain instances may range from 1.2× to 100×, such as 2× to 6×. Where the target condition is an allergy, e.g., as described below, specific IgE levels may be reduced, e.g., as determined using the assay described in the Examples Section, below. The magnitude of IgE level reduction may vary, and in certain instances may range from 1.1× to 7×, such as 2× to 6×.

As summarized above, immune mediated conditions that are the targets of methods of the invention include immune-mediated inflammatory conditions, where such conditions include, but are not limited to conditions characterized by common inflammatory pathways leading to inflammation, and which may result from, or be triggered by, a dysregulation of the normal immune response. Examples of immune-mediated inflammatory conditions include, but are not limited to: allergy, autoimmune diseases, ankylosing spondylitis, psoriasis, psoriatic arthritis, Behcet's disease, arthritis, inflammatory bowel disease (IBD), cardiovascular disease, neuromuscular disease, and infectious disease, etc.

In certain embodiments, a disclosed method comprises inhibiting symptoms of one or more food allergies in a human subject, comprising orally administering to the subject a composition comprising 2 to 20 different protein allergens. In further embodiments, a disclosed method comprises treating one or more food allergies in a human subject with an existing food allergy to one or more foods, comprising administering to the subject a composition comprising 2 to 20 different protein allergens. In certain embodiments, administration of the composition significantly inhibits the symptoms of a food allergy in the subject as compared to administering to the subject a composition that includes only one protein allergen. The one or more food allergies may be a single food allergy or a multiple food allergy. The target allergy may vary widely, where in some instances the target allergy is food allergy, drug allergy, environmental allergy, animal allergy, and insect and/or bee allergy. As such, aspects of the invention include methods of reducing the risk of a subject for developing an allergy. In certain embodiments, the methods result in the subject having a reduced risk of developing a food allergy to a food allergen that is not present in the mixed allergen composition that is administered to the subject. For example, the administered composition may provide to the subject allergen protection for a nut protein in the formulation as well as a nut protein not found in the formulation. In certain embodiments, the reduced risk for a first food allergen is reduced to a greater extent using the mixed formulation than would be achieved using a formulation with only a single allergen. For example, feeding a mixed allergen formulation as described herein can result in lower risk of allergy development for an allergen (e.g., with respect to Th2/IgE/IgG4 analyses, as shown below) than if the formulation only included that single allergen. In some cases, this phenomenon is referred to as "synergy" (e.g., cashew synergizes with pistachio, walnut with pecan, shrimp with lobster (and other crustacean), and vice-versa). Where the method is a method of treating the subject for the allergy, as reviewed above the method may result in at least an amelioration of one or more symptoms associated with the allergy, e.g., as described above. Allergy symptoms that may be ameliorated, but are not limited to: eczema, asthma, atopic dermatitis, bronchospasm, cough, rhinorrhea, angioedema, gastric hypermotility, urticaria (hives), pruritis, fatigue, bradycardia, allergic rhinitis, allergic conjunctivitis, and/or hypotension. The magnitude of the symptom reduction may vary, where in some instances the magnitude is 2-fold or greater, e.g., 5-fold or greater, including 10-fold or greater, e.g., as compared to a suitable control. In some instances, treatment of an allergy results the subject being cured of the allergy, such that the subject no longer suffers from the allergy. In some embodiments of allergy treatment methods, the methods include administering to a subject a mixed allergen composition that includes a nut allergen; an animal allergen; and at least one of: a non-nut plant allergen a biotic agent; and a vitamin, such as described above.

Also provided are methods of significantly reducing the probability of developing one or more food allergies in a subject. In certain embodiments, a subject is an unborn child of a pregnant woman or a child of nursing mother, and the method comprises administering to the pregnant or nursing mother a disclosed composition. In certain embodiments, the subject is a child having a developing immune system. Further provided are methods for desensitizing a human to one major allergen or to two or more major allergens comprising administering to the human a food product comprising two or more allergens, wherein the composition is administered according to a schedule of treatment.

In some instances, the methods are methods of treating a subject for an eosinophilic disorder. Eosinophilic disorders are disorders characterized by the occurrence of eosinophils in above-normal amounts in various parts of the body. Eosinophilic disorders of interest include, but are not limited to: eosinophilic esophagitis (esophagus); eosinophilic gastritis (stomach); eosinophilic enteritis (small intestine); eosinophilic colitis (large intestine); hypereosinophilic syndrome (blood and any organ); and the like. In some instances the methods are methods of reducing the risk of a subject for developing an eosinophilic disorder. The magnitude of the risk reduction may vary, where in some instances the magnitude is 2-fold or greater, e.g., 5-fold or greater, including 10-fold or greater, e.g., as compared to a suitable control.

In some instances the methods are methods of treating a subject for inflammation, where the inflammation may be a symptom of a variety of different disease conditions. Disease conditions in which the inflammation thereof may be treated according to embodiments of the invention include, but are not limited celiac disease, multiple sclerosis, inflammatory bowel disease, eosinophilic diseases, allergy, food allergy, etc.

Aspects of the invention further include methods of at least decreasing the potential of a fetus or suckling infant for developing an immune mediated condition, such as an immune-mediated inflammatory disease condition, e.g., allergy, such as described above. By at least decreasing the potential of the fetus or suckling infant for developing an immune mediated condition is meant that the probability of the fetus or suckling infant for developing the immune mediated condition is reduced, such that the risk of the fetus or suckling infant for developing the immune mediated condition is reduced. The magnitude of the decrease in potential may vary, where in some instances the magnitude is 2-fold or greater, e.g., 5-fold or greater, including 10-fold or greater, e.g., as compared to a suitable control. In some instances, the methods are methods of preventing the fetus or suckling infant from developing an immune mediated condition. As such, the methods of the invention include administering a composition of the invention to a mother of a fetus or suckling infant that is not known to have or does not have an immune mediated condition. While the fetus or suckling infant may not have or may not be known to have the immune mediated condition, the fetus or suckling infant may be one that is suspected to be or known to be at risk of developing the immune mediated condition.

In certain embodiments, the mixed allergen composition or physiologically acceptable composition that includes the same is administered to a pregnant or nursing mother of a pediatric subject, fetus or suckling infant. For example, the mixed allergen composition or physiologically acceptable composition that includes the same may be administered to a mother pregnant with the fetus. In such instances, the mixed allergen composition or physiologically acceptable composition that includes the same may be administered to the mother using any convenient dosing schedule, e.g., as described above, starting at any convenient time during the pregnancy, e.g., at the start of the second trimester, at the start of the third trimester, etc. Where the method is a method of reducing risk in a suckling infant, the mixed allergen composition or physiologically acceptable composition that includes the same may be administered to a mother that is breast feeding the infant. In such instances, the mixed allergen composition or physiologically acceptable composition that includes the same may be administered to the breast feeding mother using any convenient dosing schedule, e.g., as described above, starting at any convenient time during the breast feeding, e.g., at the start of lactation, 1 week after lactation commencement, etc.

Practice of the invention will be more fully understood from the foregoing examples, which are presented herein for illustrative purposes only, and should not be construed as limiting the invention in any way.

EXAMPLES

Example 1—Mixed Allergen Assay #1

Study Design and Population/Allergen Treatment

For each allergen or allergen mix listed below (the allergen groups), five subjects from each of five different age groups were fed a total of 300 mg of the allergen or allergen mix daily for one year. The only exceptions are for Formula 1 at 3× (i.e., 3× mix) and Formula 1 at 10× (i.e., 10× mix), in which the subjects were fed 900 mg and 3,000 mg of the formula on a daily basis, respectively. Allergen mixes were formulated at a 1:1 ratio. Thus, for an allergen mix with 2 allergens, the mix would include 150 mg of each. Five subjects were included in each age group that were not fed an allergen (Not Treated, or NT group, listed last in FIGS. 1-3).

The following 18 groups were randomized equally. Children ate (daily) either 1) cashew alone, 2) cashew and pistachio, 3) walnut alone, 4) walnut and pecan, 5) a protein mix containing equal parts walnut, hazelnut, shrimp, salmon, hen's egg, cow's milk, peanut, cashew, almond, and wheat (1x mix supplement at equal protein ratios), 6) a 3x mix supplement of the same proteins as the 1x mix, 7) a 10x mix supplement of the same proteins as the 1x mix, 8) control group that followed AAP guidelines prior to October 2015, 9) white fish alone 10) white fish and pink fish, 11) shrimp alone, 12) shrimp and crab, 13) peanut alone, 14) peanut and soy, 15) hazelnut alone, 16) almond alone, 17) cow's milk, 18) hen's egg, Supplement mixes were added to breast milk or to relevant food items eaten (i.e. apple sauce, pudding, shakes, yogurt) by the different age groups, eaten freshly, and parents were told to watch and document the full intake of the supplement daily. The protein mix was approximately a teaspoon daily.

Each treatment group consisted of five children from each of the following five age groups: 4 to 6 months, 7 to 12 months, 1 to 3 years, 3 to 5 years, and 5 years or older. The subjects were not selected based on observed or suspected food allergy (or other allergy) profile, and thus the cohort of subjects tested included those who may have, or have the propensity to develop, a food allergy as well as those who do not. Children were both low- and high-risk (defined by a first degree relative with atopic dermatitis or two first degree relatives with atopy) for developing allergies, but none had a doctor's diagnosis of food allergy.

Allergen or Allergen Mix/Protein Powders

The allergens included in the study were flours/dry powders from peanuts, almonds, cashews, walnut, pecan, hazelnut, wheat, soy, shrimp, salmon, hen's egg (sodium lauryl sulphate was added as an anti-caking agent), cow's milk, white fish, pink fish, sesame, and crab. The details of the allergens and allergen mixes were as follows:

1. Cashew: Finely ground cashew from "Wellbee's", Spring Valley, N.Y. 10977.
2. Cashew and pistachio (pis): Finely ground cashew from "Wellbee's", Spring Valley, N.Y. 10977. Pistachio flour from "nuts.com", Cranford, N.J. 07016.
3. Walnut: Roasted walnut from "Holmquist Hazelnut Orchards", Lynden Wash. 98264.
4. Walnut and pecan: Roasted walnut from "Holmquist Hazelnut Orchards", Lynden Wash. 98264. Ground pecan from "King Arthur Flour", Norwich, Vt., 05055.
5. Formula 1 at 1x (1x mix): equal parts walnut (Roasted walnut from "Holmquist Hazelnut Orchards", Lynden Wash. 98264), hazelnut (Natural hazelnuts from "Holmquist Hazelnut Orchards", Lynden Wash. 98264), shrimp (White shrimp from "Seattle Seafoods", Bellevue, Wash. 98008), salmon (Sockeye salmon from "Seattle Seafoods", Bellevue, Wash. 98008), hen's egg (Powdered egg whites with sodium lauryl sulphate as an anti-caking agent from "Honeyville Food Products", Honeyville, Utah 84314), cow's milk (Organic non-fat dry milk powder from "Now Foods" Bloomingdale, Ill. 60108), peanut (Defatted peanuts from "Byrd Mill Company", Ashland, Va. 23005), cashew (Finely ground cashew from "Wellbee's", Spring Valley, N.Y. 10977), almond (Blanched almond flour from "Honeyville" Rancho Cucamonga, Calif. 91730), and wheat (Wheat flour from "Arrowhead Mills", USA. Boulder, Colo. 80301) (30 mg of protein each).
6. Formula 1 at 3x (3x mix): equal parts walnut, hazelnut, shrimp, salmon, hen's egg, cow's milk, peanut, cashew, almond, and wheat as above (90 mg of each protein)
7. Formula 1 at 10x (10x mix): equal parts walnut, hazelnut, shrimp, salmon, hen's egg, cow's milk, peanut, cashew, almond, and wheat as above (300 mg of each protein)
8. Non-treated control (NT)
9. White fish: Pacific cod from "Seattle Seafoods", Bellevue, Wash. 98008.
10. White fish and pink fish: Pacific cod and sockeye salmon from "Seattle Seafoods", Bellevue, Wash. 98008.
11. Shrimp: White shrimp from "Seattle Seafoods", Bellevue, Wash. 98008.
12. Shrimp and crab: White shrimp and crab from "Seattle Seafoods", Bellevue, Wash. 98008.
13. Peanut: Defatted peanuts from "Byrd Mill Company", Ashland, Va. 23005.
14. Peanut and soy: Defatted peanuts from "Byrd Mill Company", Ashland, Va. 23005. Stone ground soy from "Bob's Red Mill", Milwaukie, Oreg. 97222.
15. Hazelnut: Natural hazelnuts from "Holmquist Hazelnut Orchards", Lynden Wash. 98264.
16. Almond: Blanched almond flour from "Honeyville" Rancho Cucamonga, Calif. 91730.
17. Milk: Organic non-fat dry milk powder from "Now Foods" Bloomingdale, Ill. 60108.
18. Egg: Powdered egg whites with sodium lauryl sulphate as an anti-caking agent from "Honeyville Food Products", Honeyville, Utah 84314.

The total dose of allergens used was 300 mg for single allergens and for allergen mixes unless specified otherwise. A 3x and 10x formulation containing 10 allergens each containing 900 mg and 3000 mg total allergen, respectively, were also used in the study. Allergen mixes were formulated so that equal amounts of each allergen were present in the mix, so for a 2 and 10 allergen-mix formulation with 300 mg total allergen, the amount of each allergen was 150 mg and 30 mg, respectively. Mixing occurred prior to ingestion.

Blood Sample Collection

Peripheral blood mononuclear cells (PBMCs) and plasma were extracted from blood via ficoll procedure and stored in liquid nitrogen and at −80° C., respectively. Allergen-specific IgE and IgG4 were measured using a standard ImmunoCAP assay (Phadia, Uppsala, Sweden).

Stimulation and Enumeration of Th2 Cell Subsets

PBMCs from subjects were labeled with carboxyfluorescein diacetate succinimidyl ester (CFSE) and cultured with the same food allergen or food allergen mix that was fed to the participant at 100 μg/mL or anti-CD3/CD28 (to test for nonspecific proliferation capacity) for 7 days to identify T cell subsets. At day 7, cells were washed and stained for surface CD4, CD25, CD127, CD45RO, CD45RA, CD40L, and CD69 and intracellular Foxp3 and IL-10 along with Live/Dead staining (Invitrogen) (see T-cell flow cytometry method below). Th2 cells were defined as the cells that proliferated in response to food allergen (CFSElo) and were CD41 IL-4, IL-13 cells. Antigen-induced T cells were also identified by isolating CD40L and CD69 double-positive cells after antigen stimulation.

T-Cell Flow Cytometry

Cells were fixed with Lyse/Fix PhosFlow buffer (BD Biosciences). For intracellular staining, fixed cells were permeabilized with Perm Buffer III (BD Biosciences) at 48° C. for 30 minutes, followed by staining at 48° C. for 20 minutes. Flow cytometry was performed with an LSRII flow cytometer (BD Biosciences). Viable cells were identified with a Live/Dead probe (Invitrogen). Phenotypes of T cells were detected with antibodies against surface CD3 (UCHT1), CD4 (51(3), CD25 (4E3), CD127 (SB199), CD45RO (UCHL1), CD45RA (HI100), CD62L (DREG-56), CCR4 (1G1), and CCR8 from BD Biosciences; CCR7, CD69, and CD40L and intracellular IL-10 (JES3-19F1), IL-4 (MP4-25D2), and IL-13 (JES10-52A2) from BD Biosciences; Helios (22F6) from BioLegend; anti-CD49b from BioLegend; anti-LAG3 from R&D Systems (Minneapolis, Minn.); and Foxp3 (150D) from BioLegend and stained per the manufacturer-recommended protocol.

Measurement of Antibody Titers

Total and allergen-specific blood IgE and IgG4 levels were measured in all subjects in the Clinical Laboratories at Stanford Hospital and Clinics using a standard ImmunoCAP assay (Phadia, Uppsala, Sweden).

Statistical Analysis

Comparisons between cohorts, and between baseline and 1 year and control groups were evaluated with the nonparametric Mann-Whitney test, paired Wilcoxon test, and 1-way and 2-way ANOVA (GraphPad Prism Software 5.0; GraphPad Software, La Jolla, Calif.), as appropriate. A P value of less than 0.05 was considered statistically significant.

Compliance and Safety

Compliance was excellent with no dropouts in control arm and fifteen drop outs in ingested arms total. Of those who completed the study, there were only 90 missed doses (out of a total of 240,810) as determined by reviews of electronic dietary records (see Table 2). Adverse events were minimal in the active with only 21 cases of mild skin rash (21/660; 0.03%). Adverse events in the control group consisted of 3 cases of mild skin rash (3/30; 10%). 15 dropped out of the study at about 1 year in the active arm due to non-compliance, not due to safety issues.

TABLE 1

Summary of adverse reactions in ingestion and control groups

| Reaction Rates | Fed | Control |
| --- | --- | --- |
| Participants (ITT analysis) | N = 660 | N = 30 |
| Ingestions completed | 240,810 (90 missed) | n/a |
| Reactions Total | 21 (0.03%) | 3 (10%) |
| Mild | 21 (skin rash) | 3 (skin rash) |
| Moderate | 0 | 0 |
| Severe | 0 | 0 |

Th2 Cell Proliferation

PBMCs from each subject in allergen groups 1 to 18 were stimulated ex vivo with the allergen or allergen mix fed to the subject for 7 days and Th2 cell proliferation was analyzed (as described above). It is noted that for Formula 1 3× and Formula 1 10× groups, the PBMCs were stimulated with 3× and 10× the amount of allergen ex vivo, respectively (i.e., 300 µg/mL and 1000 µg/mL, respectively).

As shown in FIG. 1, stimulation of PBMCs from cohorts fed single allergens or allergen mixes had a lower degree of Th2 proliferation than controls (non-treated 1-year and non-treated baseline), indicating decreases in allergic response on exposure to allergens or allergen mixes. Additionally, the allergen mixes containing 10 allergens had the lowest degree of Th2 proliferation, significantly more than that of cohorts containing allergen mixes of 2 allergens or single allergens, indicating that diversity of food proteins further decreases allergic response.

Specifically, subjects in allergen groups 1 to 4 and 9 to 18 showed a somewhat reduced Th2 proliferation in response to allergen stimulation as compared to the non-treated control (Group 8; Baseline-NT). However, Th2 cell proliferation in PBMCs from subjects in allergen groups 5 to 7 (fed increasing amounts of Formula 1), who were fed formulations having 10 separate allergens, as described above, had significantly reduced Th2 cell proliferation as compared to both the control group (NT) as well as all other antigen groups (1 to 4 and 9 to 18). This phenomenon was seen for all subjects in all allergen groups at all ages tested, including for the different doses (1×, 3×, and 10× allergen mix).

Immunoglobulin Analyses

In addition to the Th2 proliferation assay above, plasma from subjects in allergen groups 1 to 18 were analyzed for the presence of IgG4 and IgE antibodies (using standard methods, as described above), the former being an indicator of a non-allergenic or non-inflammatory (or anti-allergenic or non-inflammatory) state and the latter an indicator of pro-allergenic or pro-inflammatory a sate.

Figure 2:
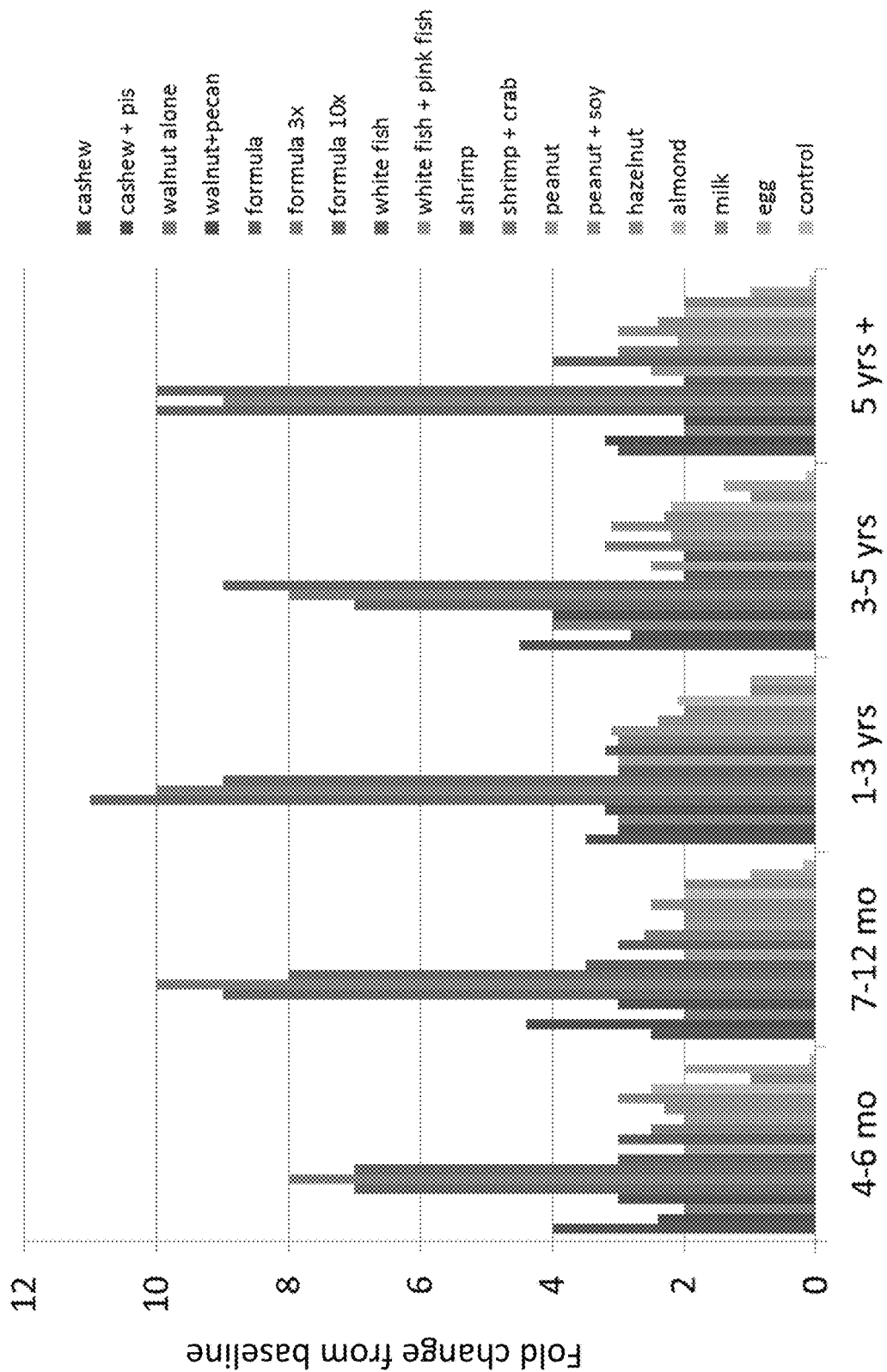
FIG. 2 depicts specific IgG4 levels in plasma from subjects fed different food allergen mixtures (units are mg IgG4/L).

Increased IgG4 levels indicate a protective anti-inflammatory state. As shown in FIG. 2, when compared to baseline, samples from participants from all cohorts showed an increase in IgG4, with the 10-allergen mix formula showing greater IgG4 levels than from those from cohorts fed single allergens or 2-allergen mixes. No significant difference in IgG4 was observed between the 1×, 3×, and 10× allergen mixes containing 10 allergens.

Specifically, subjects in allergenic groups 1 to 4 and 9 to 18 showed moderately increased levels of IgG4 as compared to the baseline group (Group 8; NT). However, allergen groups 5 to 7 (fed increasing amounts of Formula 1) showed significantly increased levels of IgG4 as compared to both the baseline group as well as all other antigen groups (1 to 4 and 8 to 18). This result is consistent with the results for Th2 cell proliferation as described above. Specifically, increased levels of IgG4 in the plasma and reduced Th2 cell proliferation are indicators of a reduced or non-allergenic or non-inflammatory state in a subject.

Figure 3:
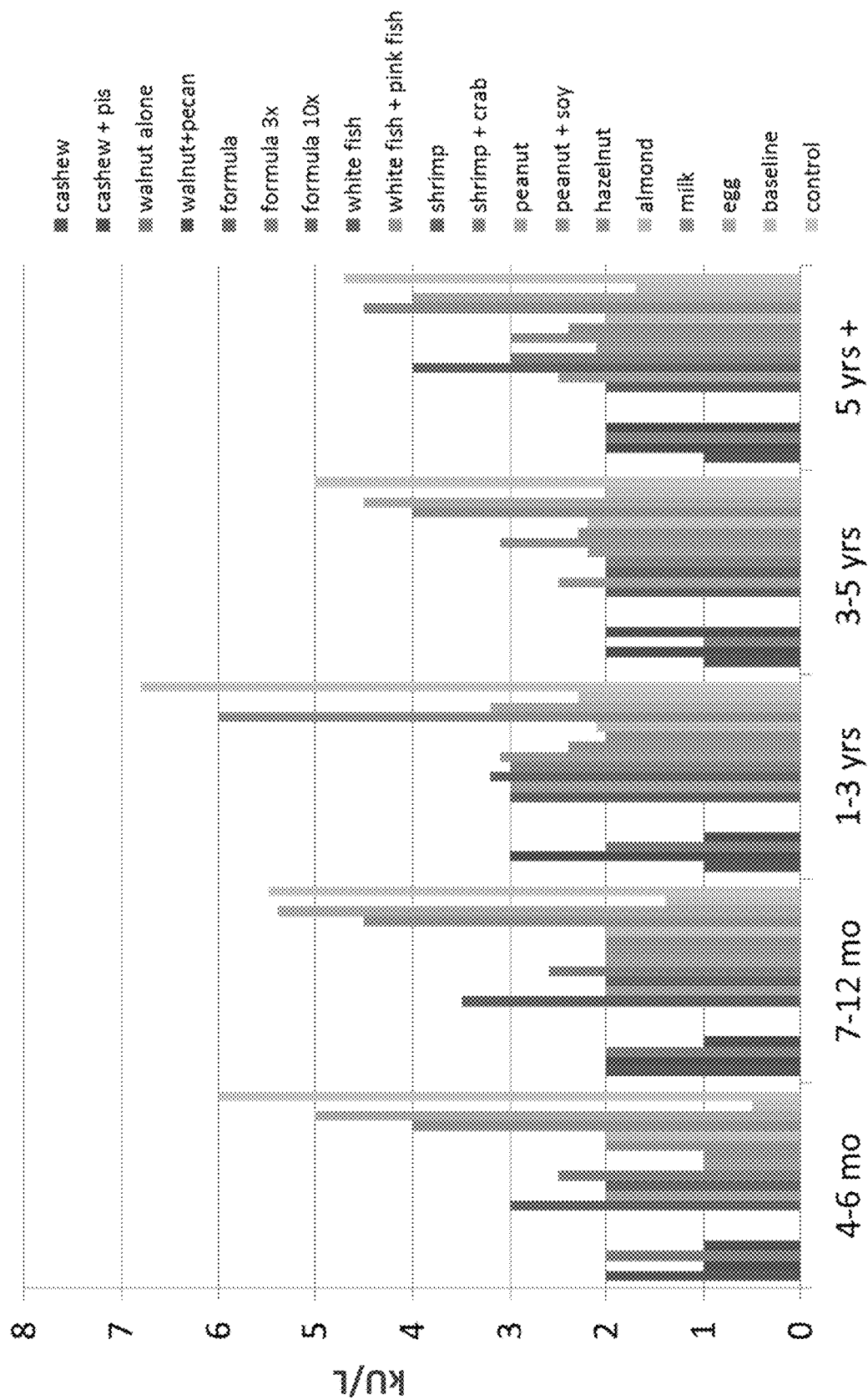
FIG. 3 depicts specific IgE levels in plasma from subjects fed different food allergen mixtures (units are mg IgE/L).

Increased specific IgE is indicative of an inflammatory allergic state. As shown in FIG. 3, samples from participants from all cohorts fed allergens or allergen mixes showed decreases in IgE, with the plasma of those fed the 10-allergen mix (1×, 3×, and 10× formulations) having IgE levels below the assay detection level. In particular, subjects in allergenic groups 1 to 4 and 9 to 17 showed significantly higher levels of IgE in the plasma as compared to allergen groups 5 to 7 (fed increasing amounts of Formula 1). Indeed, IgE levels in the allergen groups 5 to 7 were below the level of detection of the assay.

These results are consistent with the results for Th2 cell proliferation and the IgG4 levels as described above. Specifically, low levels of IgE and increased levels of IgG4 in the plasma coupled with reduced Th2 cell proliferation are indicators of a reduced or non-allergenic or non-inflammatory state in a subject.

It is clear from the results above that continual feeding of a complex mixture of food allergens to subjects (e.g., in the form of Formula 1 described above) at a very young age can prophylactically protect a subject from developing an allergenic or inflammatory immune profile to a wide variety of antigens. In other words, this process can induce in a subject a non-allergenic or non-inflammatory (or anti-allergenic or anti-inflammatory) state. Of particular interest in the results shown herein is the indication that feeding antigens in a complex mixture provides broad spectrum protection against developing allergies/inflammation that is superior to single or even double allergen formulas that target a single allergen (as in allergen groups 1, 3, 11, 13 and 15 to 18 above) or multiple related allergens (e.g., as in allergen groups 2, 4, 10, 12, and 14 above).

The above shows that feeding subjects complex antigen mixtures will not only protect against the development of allergies and/or inflammation to the allergens/antigens in the complex mixture, but also to allergens or antigens that are not present in the complex mixture. In essence, feeding complex food antigen mixtures creates a general anti-allergenic or anti-inflammatory state in a subject that broadly prevents the development of allergies or inflammatory state, even to allergens/antigens not yet fed to the subject.

Mixed Allergen Compositions (+Probiotics and/or Vitamin)

Subjects were also fed compositions comprising allergen mixes in a 1:1 blend with probiotics and/or vitamins. The details of the compositions that were used are shown below:

1. Formula 1 at 1× (equal parts walnut, hazelnut, shrimp, salmon, hen's egg, cow's milk, peanut, cashew, almond, and wheat)
2. Non-treated control (NT)
3. 1 part Formula 1 at 1× (as above) with 1 part vitamin D (400 IU; Vitamin in this instance was Poly Vi Sol brand for children).
4. 1 part Formula 1 at 1× (as above) with 1 part probiotics (Probiotic in this instance was *Lactobacillus*; Culturelle brand).
5. 1 part Formula 1 at 1× (as above) with 1 part vitamin D (400 IU; Vitamin in this instance was Poly Vi Sol brand for children) and 1 part probiotics (*Lactobacillus*; Culturelle brand).
6. 1 part Formula 1 at 1× (as above) after baking (15 min at 350° F.).
7. 1 part Formula 1 at 1× (as above) after incubation at pH=2 for 15 min.

Each composition had 300 mg each of the dietary supplement mixture, probiotics, and/or vitamins when present. Mixtures at pH 2 were incubated in vinegar for 40 min at room temperature before using. Mixtures that were baked were heated for 40 min at 350° F. Control received no dietary supplement.

T-Cell Proliferation

Figure 4:
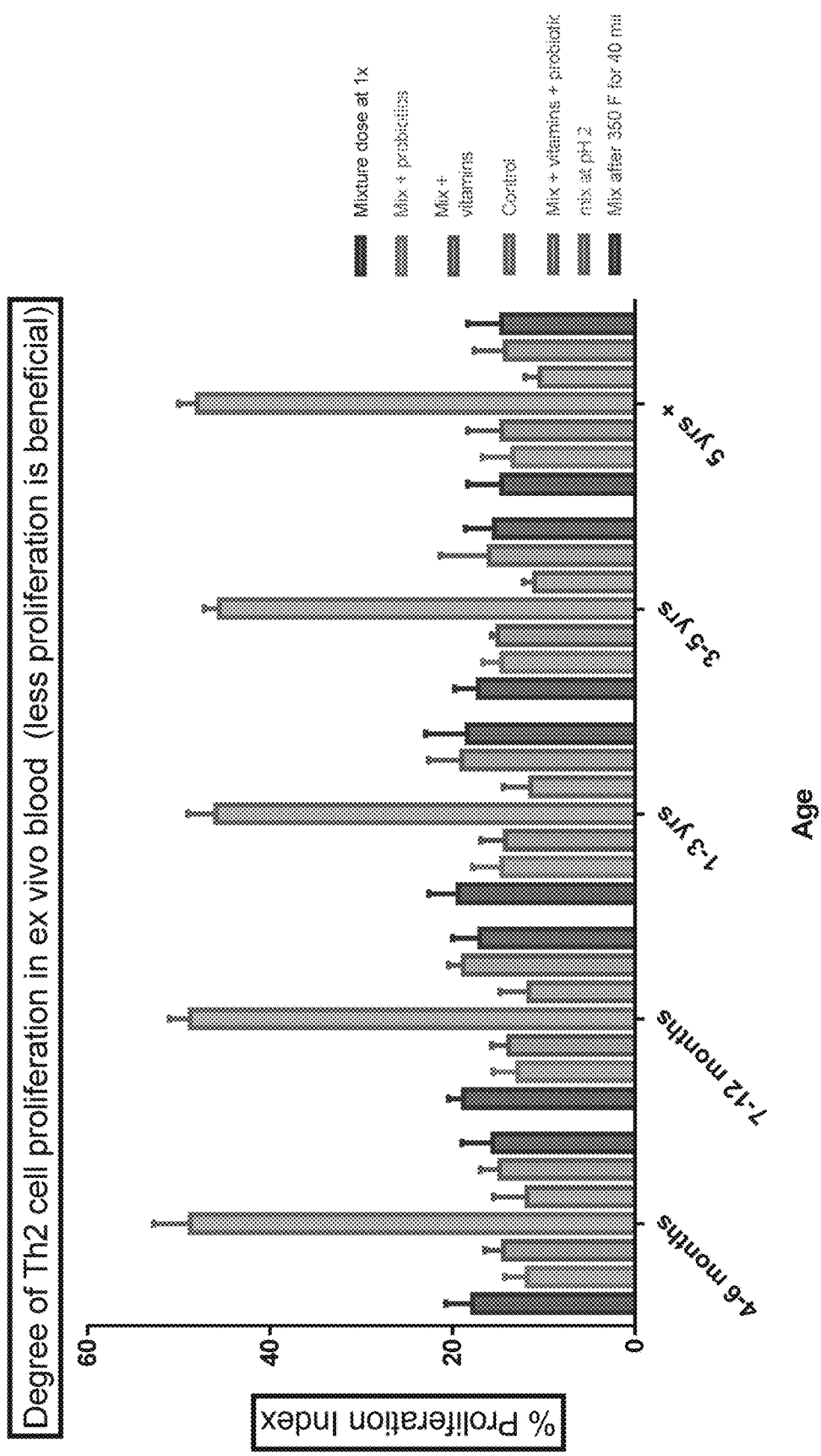
FIG. 4 depicts Th2 cell proliferation in ex vivo blood samples from subjects fed different food allergen mixtures (units are cells/mL).

PBMCs from each subject were stimulated ex vivo with the allergen or mixed compositions described above and Th2 cell proliferation was analyzed as described above. As shown in FIG. 4, PBMCs on stimulation ex vivo with the allergen or allergen mix under the following conditions showed similar Th2 proliferation: lower pH, addition of probiotics, addition of vitamin D, or after baking.

Subject samples showed similar Th2 proliferation decreases with the mixture or under different conditions with the mixture. This phenomenon was seen for all subjects in all allergen groups and at all ages tested.

Immunoglobulin Analyses

In addition to the Th2 proliferation assay above, plasma from subjects in allergen groups were analyzed for the presence of IgG4 and IgE antibodies (using standard methods, as described above), the former being an indicator of a non-allergenic or non-inflammatory (or anti-allergenic or anti-inflammatory) state and the latter an indicator of pro-allergenic or pro-inflammatory state.

Figure 5:
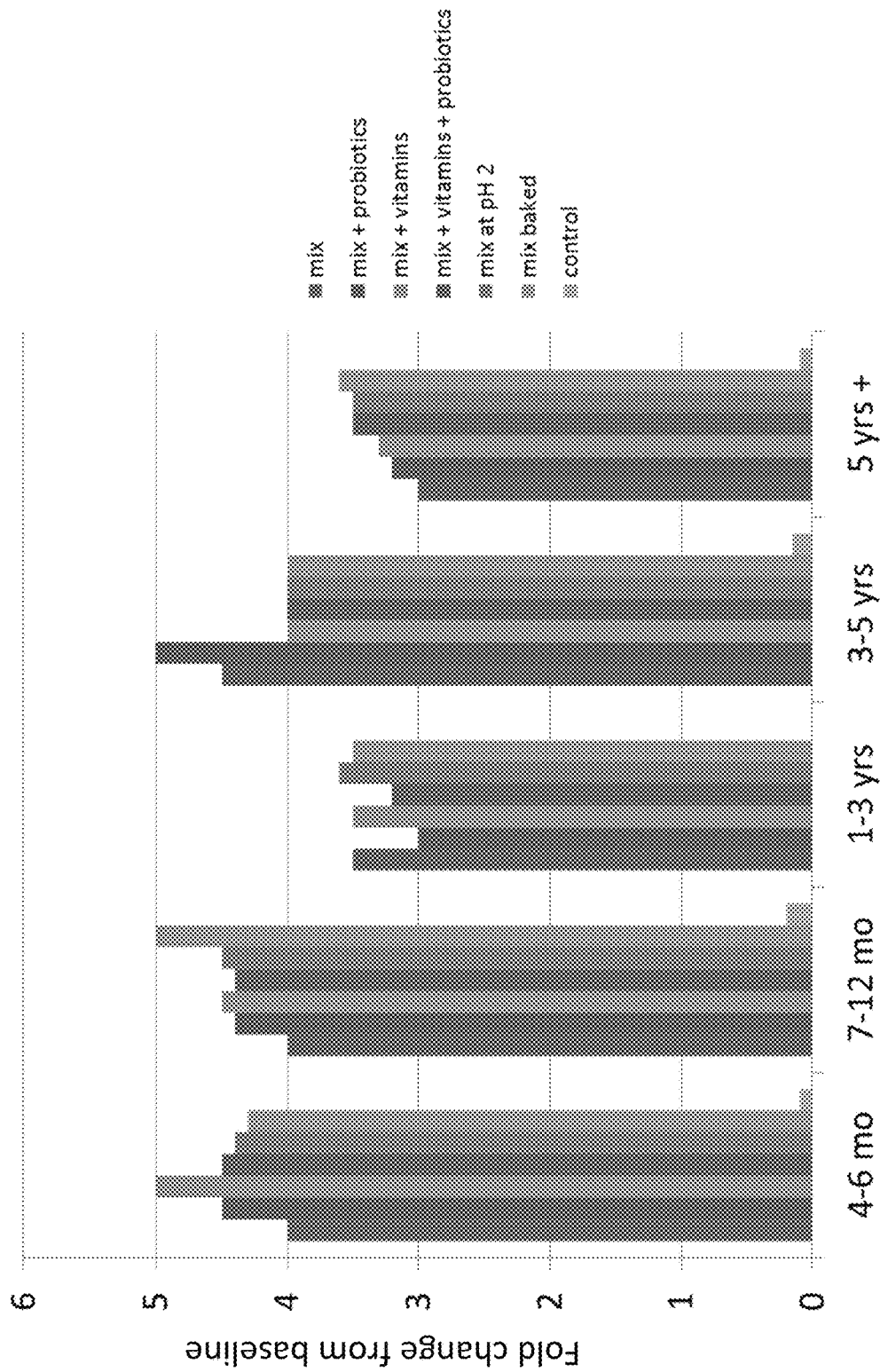
FIG. 5 depicts specific IgG4 levels in plasma from subjects fed different food allergen mixtures (units are mg IgG4/L).
Figure 6:
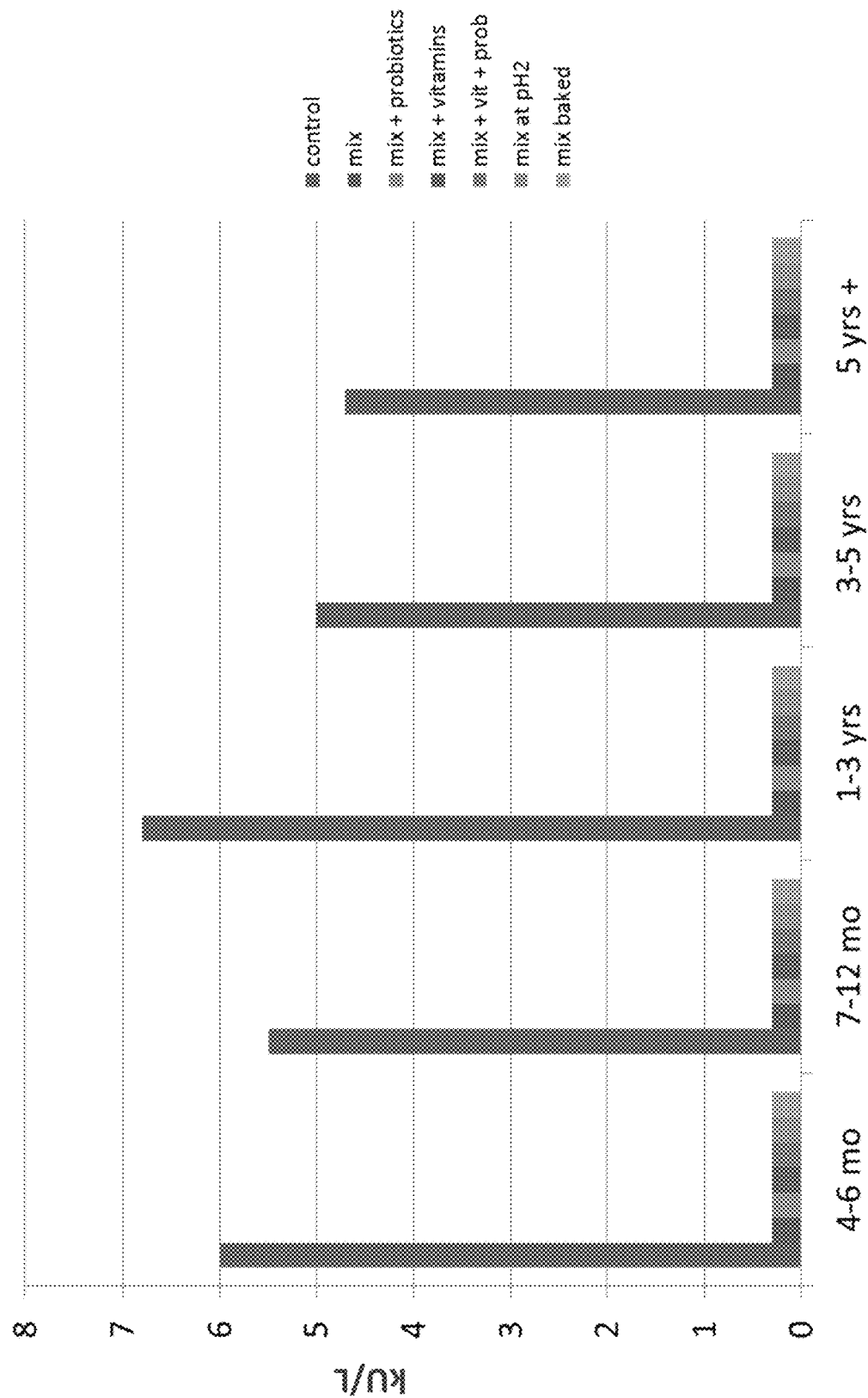
FIG. 6 depicts specific IgE levels in plasma from subjects fed the food allergen mixtures (units are mg IgE/L).

As shown in FIGS. 5 and 6, subjects showed moderately increased levels of IgG4 as compared to control group and significantly higher levels of IgE in the plasma. As shown in FIG. 5, similar IgG4 levels were observed under the following different conditions with the allergen-mix: lower pH, addition of probiotics, addition of vitamin D, or after baking. As shown in FIG. 6, no IgE levels were observed in response to the different tested mixed allergen compositions. There were similar effects seen with the mixture or under different conditions with the mixture, with similar IgE levels observed under the following different conditions with the allergen-mix: lower pH, addition of probiotics, addition of vitamin D, or after baking.

T-Cell Proliferation

Figure 7:
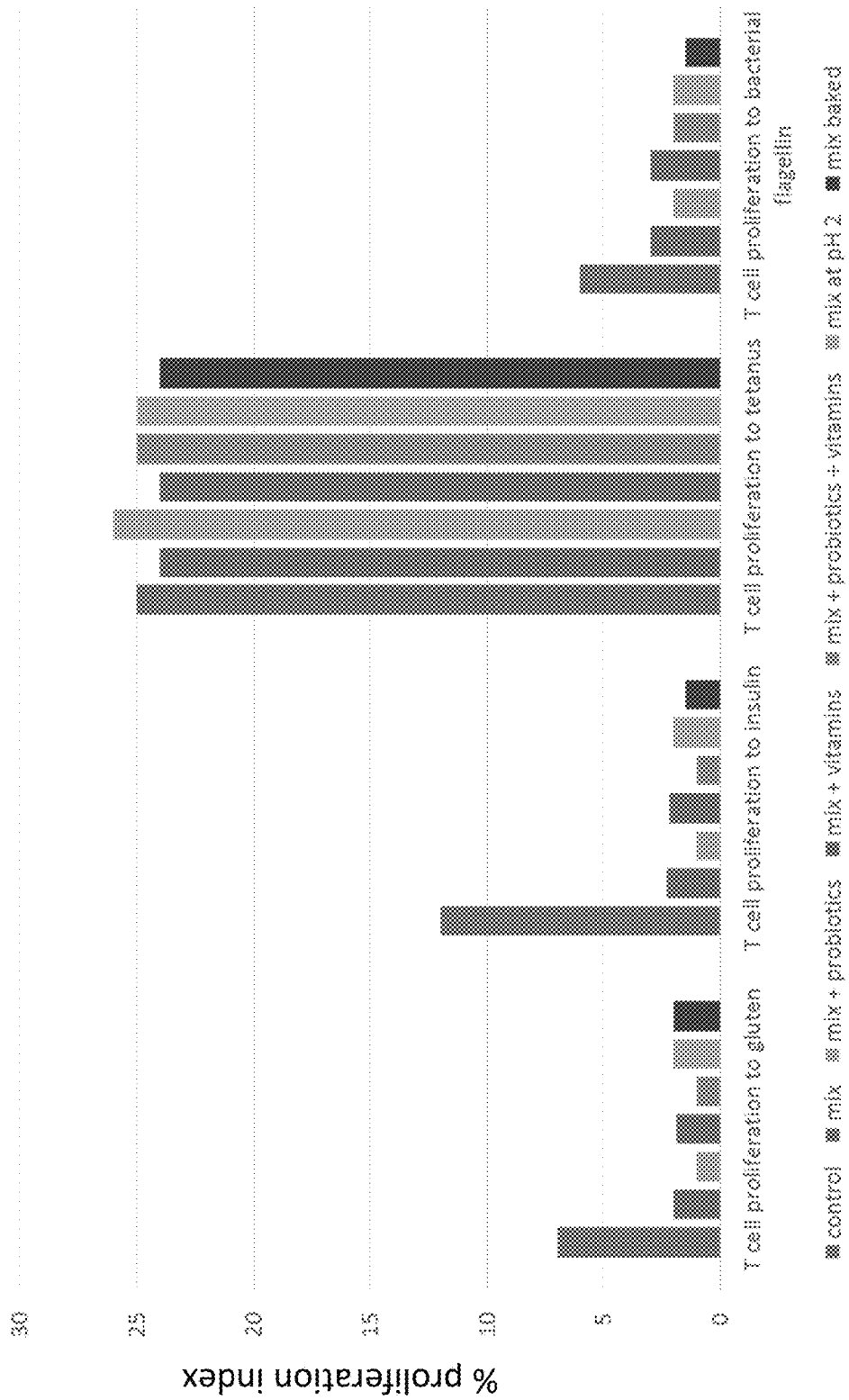
FIG. 7 depicts T cell proliferation in response to gluten, insulin, tetanus and bacterial flagellin in ex vivo blood samples from subjects fed different food allergen mixtures.

T cell proliferation was performed (please see methods section above) and data presented in FIG. 7. The data show anti-inflammatory properties to gluten (i.e., celiac agent), and insulin (i.e., diabetes agent) and bacterial flagellin (inflammatory bowel disease agent). This demonstrates that the mixture could also decrease inflammatory states involved in diseases like celiac, diabetes and inflammatory bowel diseases.

Example 2—Mixed Allergen Assay #2

Study Design and Population/Allergen Treatment

Infants and children were seen in a research setting from 4 weeks old to 3 years of age. A single allergen or allergen mix supplement was consumed orally daily for one year. Subjects were fed a total of 300 mg of a single allergen or allergen mix daily for one year. The only exceptions are for Formula 1 at 3× (i.e., 3× mix) and Formula 1 at 10× (i.e., 10× mix), in which the subjects were fed 900 mg and 3,000 mg of the formula on a daily basis, respectively. Allergen mixes were formulated at a 1:1 ratio. Thus, for an allergen mix with 2 allergens, the mix would include 150 mg of each. Thirty subjects were included that were not fed an allergen (control group listed).

There was similar distribution of age and sex, and all children were breast fed for at least the first 4 months of life. There was similar distribution of high risk and low risk for food allergy (i.e. high risk are those infants born to a family with one first degree relative with food allergy or one first degree relative with atopic dermatitis or two first degree relatives with atopic disease). None had a doctor's diagnosis of food allergy.

The subjects were not selected based on observed or suspected food allergy (or other allergy) profile, and thus the cohort of subjects tested included those who may have, or have the propensity to develop, a food allergy as well as those who do not. The total number of subjects was 60 including control.

TABLE 2

Demographics

| Age at screening | Control (n = 30) | Fed Allergen (n = 30) |
|---|---|---|
| 1 mo-3 yrs, median (SD) | 8 months (5 mo) | 9 months (6 mo) |
| High risk* | 17/30 | 18/30 |

*Defined by first degree relative with atopic dermatitis or two first degree relatives with atopy Allergen or Allergen Mix/Protein Powders The allergens included in the study were flours/dry powders from peanuts, almonds, cashews, walnut, pecan, hazelnut, wheat, soy, shrimp, salmon, hen's egg (sodium lauryl sulphate was added as an anti-caking agent), cow's milk, white fish, pink fish, and sesame. The details of the allergens and allergen mixes were as follows:

1. Formula 1 at 1× (1× mix): equal parts peanuts (Defatted peanuts from "Byrd Mill Company", Ashland, Va. 23005), almonds (Blanched almond flour from "Honeyville" Rancho Cucamonga, Calif. 91730), cashews (Finely ground cashew from "Wellbee's", Spring Valley, N.Y. 10977), walnut (Roasted walnut from "Holmquist Hazelnut Orchards", Lynden Wash. 98264), pecan (Ground pecan from "King Arthur Flour", Norwich, Vt., 05055), hazelnut (Natural hazelnuts from "Holmquist Hazelnut Orchards", Lynden Wash. 98264), wheat (Wheat flour from "Arrowhead Mills", Boulder, Colo. 80301), soy (Stone ground soy from "Bob's Red Mill", Milwaukie, Oreg. 97222), shrimp (White shrimp from "Seattle Seafoods", Bellevue, Wash. 98008), hen's egg (Powdered egg whites with sodium lauryl sulphate as an anti-caking agent from "Honeyville Food Products", Honeyville, Utah 84314), cow's milk (Organic non-fat dry milk powder from "Now Foods" Bloomingdale, Ill. 60108, white fish (Pacific cod from "Seattle Seafoods", Bellevue, Wash. 98008), pink fish (Pacific salmon from "Seattle Seafoods", Bellevue, Wash. 98008), and sesame (Sesame flour from "Dipasa", Brownsville, Tex. 78526), (30 mg of protein each) with or without vitamin D3 (400 IU). (i.e. Early Adaptive Tolerance Blend)

2. Formula 1 at 3× (3× mix): equal parts as above (90 mg of each protein) with or without vitamin D3 (400 IU). (i.e. Early Adaptive Tolerance Blend)

3. Formula 1 at 10× (10× mix): equal parts as above (300 mg of each protein) with or without vitamin D3 (400 IU). (i.e. Early Adaptive Tolerance Blend)

4. Peanut: Defatted peanuts from "Byrd Mill Company", Ashland, Va. 23005.

5. Peanut and egg: Defatted peanuts from "Byrd Mill Company", Ashland, Va. 23005, Powdered egg whites with sodium lauryl sulphate as an anti-caking agent from "Honeyville Food Products", Honeyville, Utah 84314.

6. Milk: Organic non-fat dry milk powder from "Now Foods" Bloomingdale, Ill. 60108.

7. Control

The total dose of allergens used was about 300 mg total for single allergens and for allergen mixes unless specified otherwise. A 3× and 10× formulation containing allergens each containing about 900 mg and 3000 mg total allergen, respectively, were also used in the study. Allergen mixes were formulated so that equal amounts of each allergen were present in the mix. Mixing occurred prior to ingestion.

Blood Sample Collection

Peripheral blood mononuclear cells (PBMCs) and plasma were extracted from blood via ficoll procedure and stored in liquid nitrogen and at −80° C., respectively. Allergen-specific IgE and IgG4 were measured using a standard ImmunoCAP assay (Phadia, Uppsala, Sweden).

Stimulation and Enumeration of Th2 Cell Subsets

PBMCs were labeled with carboxyfluorescein diacetate succinimidyl ester (CFSE) and cultured with the same food allergen or food allergen mix at 100 μg/mL or anti-CD3/CD28 (to test for nonspecific proliferation capacity) for 7 days to identify T cell subsets. At day 7, cells were washed and stained for surface CD4, CD25, CD127, CD45RO, CD45RA, CD40L, and CD69 and intracellular Foxp3 and IL-10 along with Live/Dead staining (Invitrogen). Th2 cells were defined as the cells that proliferated in response to food allergen (CFSElo) and were CD41 IL-4, IL-13 cells. Antigen-induced T cells were also identified by isolating CD40L and CD69 double-positive cells after antigen stimulation.

Measurement of Antibody Titers

Total and allergen-specific blood IgE and IgG4 levels were measured using a standard ImmunoCAP assay (Phadia, Uppsala, Sweden).

Statistical Analysis

Comparisons between cohorts, and between baseline and 1 year and control groups were evaluated with the nonparametric Mann-Whitney test, paired Wilcoxon test, and 1-way ANOVA (GraphPad Prism Software 5.0; GraphPad Software, La Jolla, Calif.), as appropriate. A P value of less than 0.05 was considered statistically significant.

Compliance and Safety

Compliance was excellent with no dropouts in control arm or fed arm. Of those who completed the study, there were only 3 missed doses (out of a total of approximately 10,950) as determined by reviews of electronic dietary records (see Table 3). Adverse events were minimal in the fed arm with only 2 cases of mild skin rash (2/30; 7%). Adverse events in the control group consisted of 5 cases of mild skin rash (5/30; 17%).

TABLE 3

Summary of adverse reactions in ingestion and control groups

| Reaction Rates | Fed | Control |
| --- | --- | --- |
| Participants (ITT analysis) | N = 30 | N = 30 |
| Ingestions completed | 10,950 (3 missed doses) | n/a |
| Reactions Total | 2 (7%) | 5 (17%) |
| Mild | 2 (skin rash) | 5 (skin rash) |
| Moderate | 0 | 0 |
| Severe | 0 | 0 |

Th2 Cell Proliferation

PBMCs were stimulated ex vivo with the an allergen or allergen mix fed to the subject for 7 days and Th2 cell proliferation was analyzed (as described in the Methods section above). It is noted that for Formula 1 3× and Formula 1 10×, the PBMCs were stimulated with 3× and 10× the amount of allergen ex vivo, respectively (i.e., 300 μg/mL and 1000 μg/mL, respectively).

Figure 8:
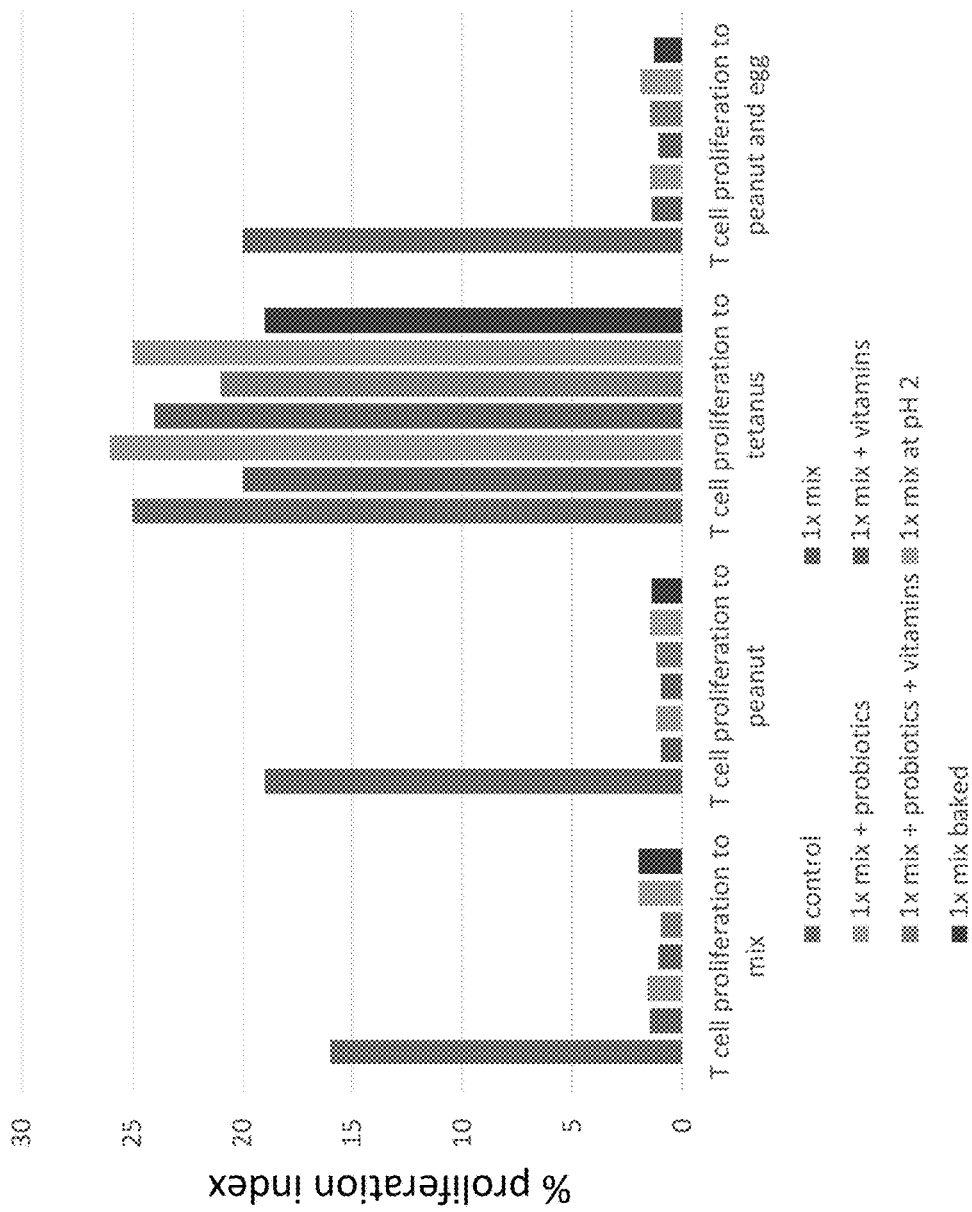
FIG. 8 depicts Th2 cell proliferation in ex vivo blood samples from subjects fed different food allergen mixtures (units are cells/mL).

As shown in FIG. 8, PBMCs from fed subjects stimulated with single allergens or allergen mixes had a lower degree of Th2 proliferation than stimulated PBMCs from control subjects, indicating decreases in allergic response on exposure to the allergen mixes.

Immunoglobulin Analyses

In addition to the Th2 proliferation assay above, plasma from subjects were analyzed for the presence of IgG4 and IgE specific antibodies (using standard methods, as described above), the former being an indicator of a non-allergenic or non-inflammatory (or anti-allergenic or non-inflammatory) state and the latter an indicator of pro-allergenic or pro-inflammatory state.

Figure 9:
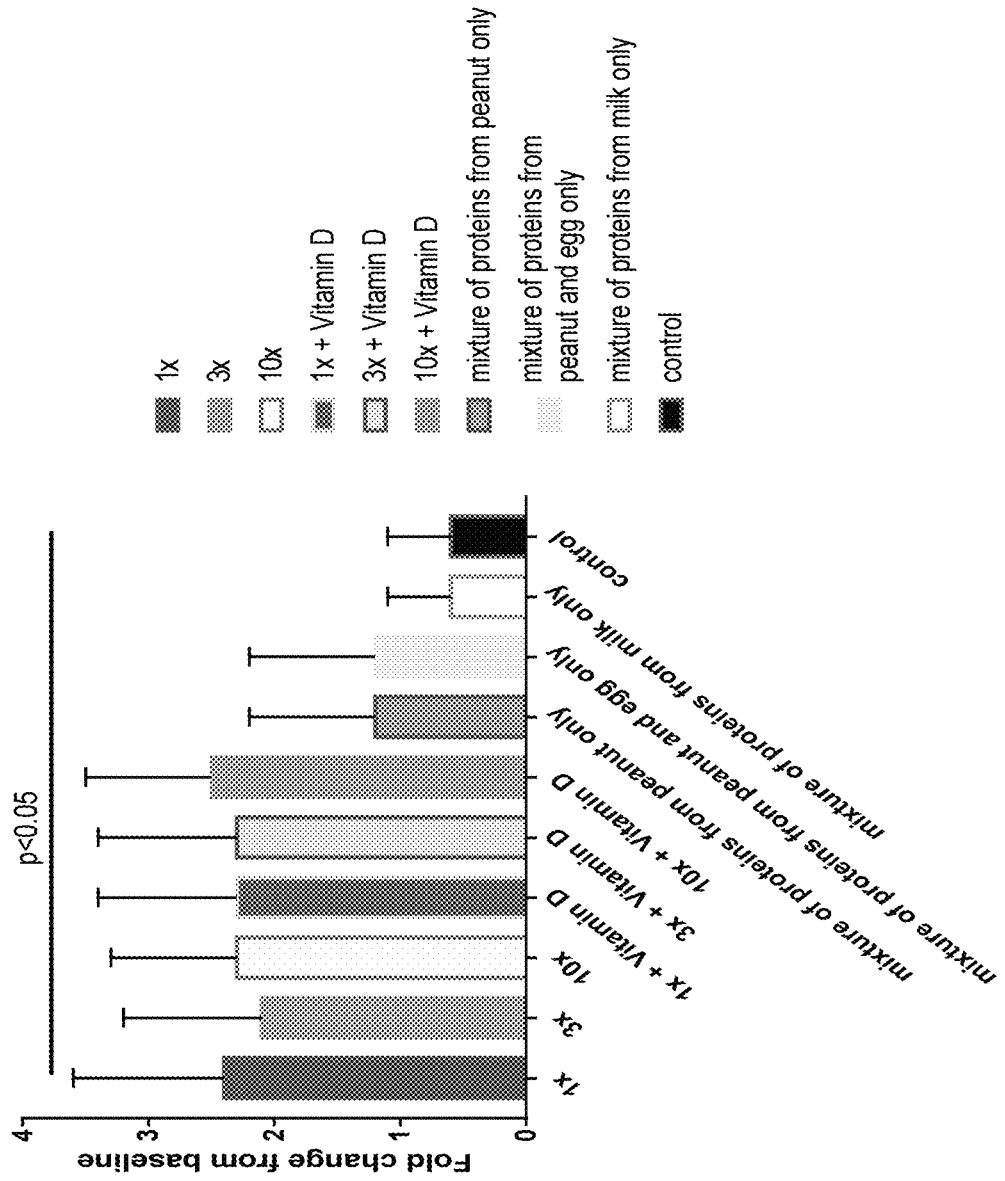
FIG. 9 depicts specific IgG4 levels in plasma from subjects fed different food allergen/mixtures (units are mg IgG4/L).

Increased IgG4 levels indicate a protective anti-inflammatory state. As shown in FIG. 9, when compared to baseline, samples from fed participants showed an increase in IgG4, with samples from participants fed the allergen mix formula showing greater IgG4 levels than those from cohorts fed single or double food compositions. No significant difference in IgG4 was observed between samples from participants fed the 1×, 3×, and 10× allergen mixes or with vitamin D3.

Figure 10:
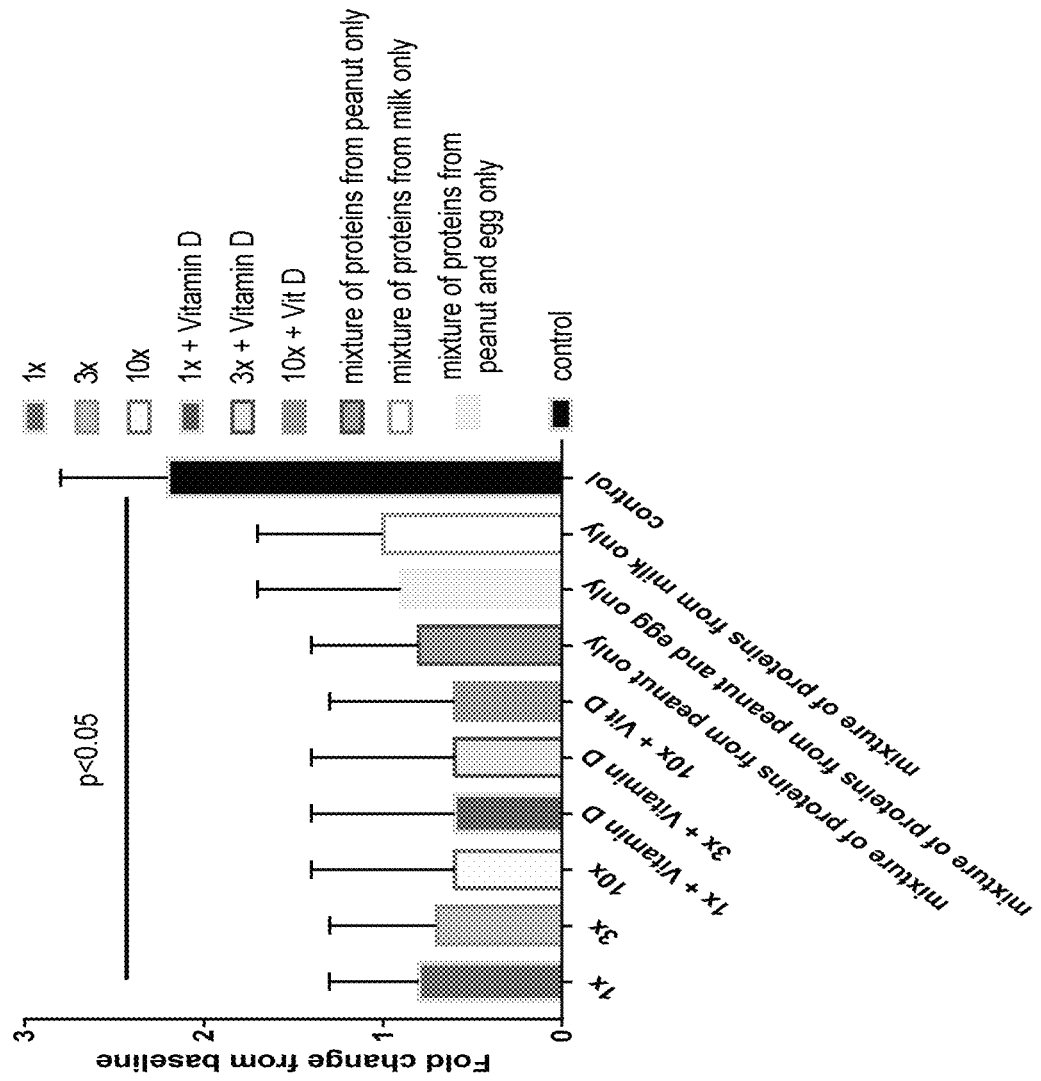
FIG. 10 depicts specific IgE levels in plasma from subjects fed different food allergen/mixtures (units are mg IgE/L).

Increased specific IgE is indicative of an inflammatory allergic state. As shown in FIG. 10, samples from participants fed single food and food mixes showed decreases in IgE, with the lowest levels seen for samples from participants fed the 1×, 3×, and 10× allergen mixes.

These results are consistent with the results for Th2 cell proliferation and the IgG4 levels as described above. Specifically, low levels of IgE and increased levels of IgG4 in the plasma coupled with reduced Th2 cell proliferation are indicators of a reduced or non-allergenic or non-inflammatory state in a subject. It is clear from the results above that continual feeding of a simple or complex mixture of food allergens to subjects (e.g., in the form of Formula 1) at a very young age can prophylactically protect a subject from developing an allergenic or inflammatory immune profile to a wide variety of antigens. In other words, this process can induce in a subject a non-allergenic or non-inflammatory (or anti-allergenic or anti-inflammatory) state. Although a single allergen product showed evidence of effect, of particular interest in the results shown herein is the indication that feeding antigens in a complex mixture provides broad spectrum protection against developing allergies/inflammation that is superior to single or even double allergen formulas that that target a single allergen.

The above shows that feeding subjects simple or complex antigen mixtures will not only protect against the development of allergies and/or inflammation to the allergens/antigens in the complex mixture, but also to allergens or antigens that are not present in the complex mixture. In essence, feeding complex food antigen mixtures creates a general anti-allergenic or anti-inflammatory state in a subject that broadly prevents the development of allergies or inflammatory state, even to allergens/antigens not yet fed to the subject.

Example 3—Therapeutic Applications of Mixed Allergen Compositions

The mixed allergen compositions disclosed herein will be further tested for their ability to treat or prevent a range of allergic diseases, e.g., asthma, atopic dermatitis, allergic rhinitis, allergic conjunctivitis, food allergies, insect allergies, or drug allergies.

The mixed allergen compositions will be given to subjects via different routes, e.g., orally, mucosal, subcutaneously, or cutaneously. Therapy will be daily or weekly, starting at small amounts (about 1 mg or less). As appropriate, it will be possible to stay on the same amount or increase by 5-100% each week, over time, to larger amounts (about 300 mg or higher). Blood from subjects will be collected at baseline and then during and after therapy. Biomarkers would be predicted to show improved immune balance and immune protection against allergy inflammation. For example, Th2 proliferation and/or IgE to the antigen would decrease and IgG4 could increase over time during the exposure to the mixed allergen compositions.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for treating a food allergy in a subject suffering from multiple food allergies, the method comprising orally administering to the subject a mixed allergen composition comprising:
    about 0.1% to about 15% by weight walnut complete allergen;
    about 0.1% to about 15% by weight peanut complete allergen;
    about 0.1% to about 15% by weight hazelnut complete allergen;
    about 0.1% to about 15% by weight soy complete allergen; and
    about 0.1% to about 15% by weight white fish complete allergen and/or pink fish complete allergen; wherein the weight is per total mass of the mixed allergen composition.

2. The method of claim 1, wherein the mixed allergen composition further comprises about 0.1% to about 15% by weight sesame complete allergen.

3. The method of claim 1, wherein the mixed allergen composition further comprises about 0.1% to about 15% by weight crustacean complete allergen.

4. The method of claim 1, wherein the mixed allergen composition comprises about 0.1% to about 15% by weight white fish complete allergen and about 0.1% to about 15% by weight pink fish complete allergen.

5. The method of claim 1, wherein the mixed allergen composition further comprises about 0.1% to about 15% by weight egg white complete allergen.

6. The method of claim 1, wherein the mixed allergen composition further comprises about 0.1% to about 15% by weight wheat complete allergen.

7. The method of claim 1, wherein the mixed allergen composition further comprises about 0.1% to about 15% by weight almond complete allergen.

8. The method of claim 1, wherein the mixed allergen composition further comprises about 0.1% to about 15% by weight oat complete allergen.

9. The method of claim 1, wherein the mixed allergen composition further comprises about 0.1% to about 15% by weight pecan complete allergen and/or about 0.1% to about 15% by weight pistachio complete allergen.

10. A method for treating a food allergy in a subject suffering from one food allergy, the method comprising orally administering to the subject a mixed allergen composition comprising:
    about 0.1% to about 15% by weight peanut complete allergen;
    about 0.1% to about 15% by weight tree nut complete allergen; and
    about 0.1% to about 15% by weight white fish complete allergen and/or pink fish complete allergen and/or crustacean complete allergen; wherein the weight is per total mass of the composition.

11. The method of claim 10, wherein the one food allergy is a peanut allergy.

12. The method of claim 10, wherein the one food allergy is a fish allergy.

13. The method of claim 10, wherein the one food allergy is a tree nut allergy.

14. The method of claim 10, wherein the mixed allergen composition further comprises about 0.1% to about 15% by weight walnut complete allergen and/or about 0.1% to about 15% by weight almond complete allergen and/or about 0.1% to about 15% by weight hazelnut complete allergen and/or about 0.1% to about 15% by weight cashew complete allergen and/or about 0.1% to about 15% by weight pecan complete allergen, wherein the weight is per total mass of the composition.

15. The method of claim 10, where the mixed allergen composition comprises about 0.1% to about 15% by weight white fish complete allergen and about 0.1% to about 15% by weight pink fish complete allergen.

16. The method of claim 15, wherein the mixed allergen composition comprises about 0.1% to about 15% by weight shrimp complete allergen.

* * * * *